(12) United States Patent
Johnson et al.

(10) Patent No.: US 11,415,251 B2
(45) Date of Patent: Aug. 16, 2022

(54) COUPLING ASSEMBLY WITH RETAINING CLIP MEMBER

(71) Applicant: Colder Products Company, Roseville, MN (US)

(72) Inventors: Robert Keith Johnson, Blaine, MN (US); Grant A. Wilhelm, Plymouth, MN (US); Elizabeth J. Langer, Minneapolis, MN (US)

(73) Assignee: Colder Products Company, Roseville, MN (US)

( * ) Notice: Subject to any disclaimer, the term of this patent is extended or adjusted under 35 U.S.C. 154(b) by 0 days.

(21) Appl. No.: 17/090,209

(22) Filed: Nov. 5, 2020

(65) Prior Publication Data

US 2021/0054955 A1  Feb. 25, 2021

Related U.S. Application Data

(63) Continuation of application No. 16/207,787, filed on Dec. 3, 2018, now Pat. No. 10,837,583, which is a
(Continued)

(51) Int. Cl.
*F16L 21/08* (2006.01)
*F16L 37/14* (2006.01)
(Continued)

(52) U.S. Cl.
CPC ........... *F16L 21/08* (2013.01); *A61M 39/105* (2013.01); *A61M 39/1011* (2013.01);
(Continued)

(58) Field of Classification Search
CPC ... Y10T 137/9029; F16L 21/08; F16L 29/007; F16L 37/08; F16L 37/144; F16L 37/38;
(Continued)

(56) References Cited

U.S. PATENT DOCUMENTS

| 2,538,259 A | 1/1951 | Merriman |
| 2,638,915 A | 5/1953 | Mitchell |

(Continued)

FOREIGN PATENT DOCUMENTS

| CN | 1676982 | 10/2005 |
| CN | 102753876 | 10/2012 |

(Continued)

OTHER PUBLICATIONS

Chinese Office Action in Chinese Application No. 2015800510717, dated Jun. 28, 2018, 15 pages, with English Translation.
(Continued)

*Primary Examiner* — Craig M Schneider
*Assistant Examiner* — Frederick D Soski
(74) *Attorney, Agent, or Firm* — Fish & Richardson P.C.

(57) ABSTRACT

A female coupling device includes: a main body, and a clip member coupled to the main body, the clip member having a plurality of arms extending perpendicularly therefrom, with the plurality of arms forming at least one pair of arms, with the pair of arms including a first distance therebetween and a second distance therebetween, with the first distance being sized to engage a clip groove of a mating male coupling device, and with the second distance being sized to disengage the mating male coupling device. In a locked position, the pair of arms is positioned so that the first distance is adjacent to the mating male coupling device. In an unlocked position, the pair of arms is positioned so that the second distance is adjacent to the mating male coupling device.

9 Claims, 36 Drawing Sheets

Related U.S. Application Data continuation of application No. 14/878,464, filed on Oct. 8, 2015, now Pat. No. 10,151,409.

(60) Provisional application No. 62/102,841, filed on Jan. 13, 2015, provisional application No. 62/061,791, filed on Oct. 9, 2014.

(51) Int. Cl.
| | |
|---|---|
| *F16L 37/56* | (2006.01) |
| *A61M 39/10* | (2006.01) |
| *F16L 29/00* | (2006.01) |
| *F16L 37/08* | (2006.01) |
| *F16L 37/38* | (2006.01) |
| *F16L 55/07* | (2006.01) |
| *F16L 3/237* | (2006.01) |

(52) U.S. Cl.
CPC ............. *F16L 29/007* (2013.01); *F16L 37/08* (2013.01); *F16L 37/144* (2013.01); *F16L 37/38* (2013.01); *F16L 37/56* (2013.01); *F16L 55/07* (2013.01); *A61M 2039/1016* (2013.01); *A61M 2039/1027* (2013.01); *F16L 3/237* (2013.01); *Y10T 137/9029* (2015.04)

(58) Field of Classification Search
CPC ........... F16L 37/56; F16L 55/07; F16L 3/237; A61M 39/1011; A61M 39/105; A61M 2039/1016; A61M 2039/1027
USPC .............................................. 251/142–149.7
See application file for complete search history.

(56) References Cited

U.S. PATENT DOCUMENTS

| | | | |
|---|---|---|---|
| 2,930,633 | A | 3/1960 | Ethington |
| 4,116,476 | A | 9/1978 | Porter |
| 4,561,682 | A | 12/1985 | Tisserat |
| 4,753,268 | A | 6/1988 | Palau |
| 4,982,736 | A | 1/1991 | Schneider |
| D319,312 | S | 8/1991 | Schneider |
| 5,169,178 | A | 12/1992 | Hunzinger |
| 5,201,552 | A | 4/1993 | Hohmann |
| 5,251,661 | A | 10/1993 | Hugues |
| 5,323,808 | A | 6/1994 | Shimizu |
| 5,332,268 | A | 7/1994 | Godeau |
| 5,354,103 | A | 10/1994 | Torrence |
| 5,415,437 | A | 5/1995 | Asou |
| 5,452,924 | A | 9/1995 | Kujawski |
| 5,464,042 | A | 11/1995 | Haunhorst |
| 5,464,256 | A | 11/1995 | Godeau |
| 5,507,529 | A | 4/1996 | Martins |
| 5,586,792 | A | 12/1996 | Kalahasthy |
| 6,302,147 | B1 | 10/2001 | Rose |
| 8,678,325 | B2 | 3/2014 | Arzate-Engels |
| 9,046,205 | B2 | 6/2015 | Whitaker |
| 9,347,594 | B2 | 5/2016 | Rusconi |
| 9,388,929 | B2 | 7/2016 | Lewis |
| 2005/0218650 | A1 | 10/2005 | Pepe |
| 2008/0012313 | A1 | 1/2008 | Reinholtz |
| 2011/0210541 | A1 | 9/2011 | Lewis |
| 2014/0261747 | A1 | 9/2014 | Bares |
| 2015/0000096 | A1* | 1/2015 | Gilbreath .............. F16L 19/005 29/426.1 |
| 2015/0377396 | A1 | 12/2015 | Rosin |
| 2016/0201835 | A1 | 7/2016 | Jones |

FOREIGN PATENT DOCUMENTS

| | | |
|---|---|---|
| CN | 103975186 | 8/2014 |
| DE | 20011475 | 9/2000 |
| EP | 2766650 | 8/2014 |
| FR | 2793867 | 11/2000 |
| FR | 2883952 | 10/2006 |
| WO | WO 2007002893 | 1/2007 |
| WO | WO 2011079228 | 6/2011 |

OTHER PUBLICATIONS

Colder Products Company, Excerpt from Quick Couplings & Fittings for Plastic Tubing, Copyright 2010, 11 pages.
EP Examination Report in Appln. No. 15787759.8, dated Nov. 12, 2019, 8 pages.
International Search Report and Written Opinion in PCT/US2015/054691, dated Jan. 29, 2016, 11 pages.
International Preliminary Report on Patentability in Application No. PCT/US2015/054691, dated Apr. 11, 2017.

* cited by examiner

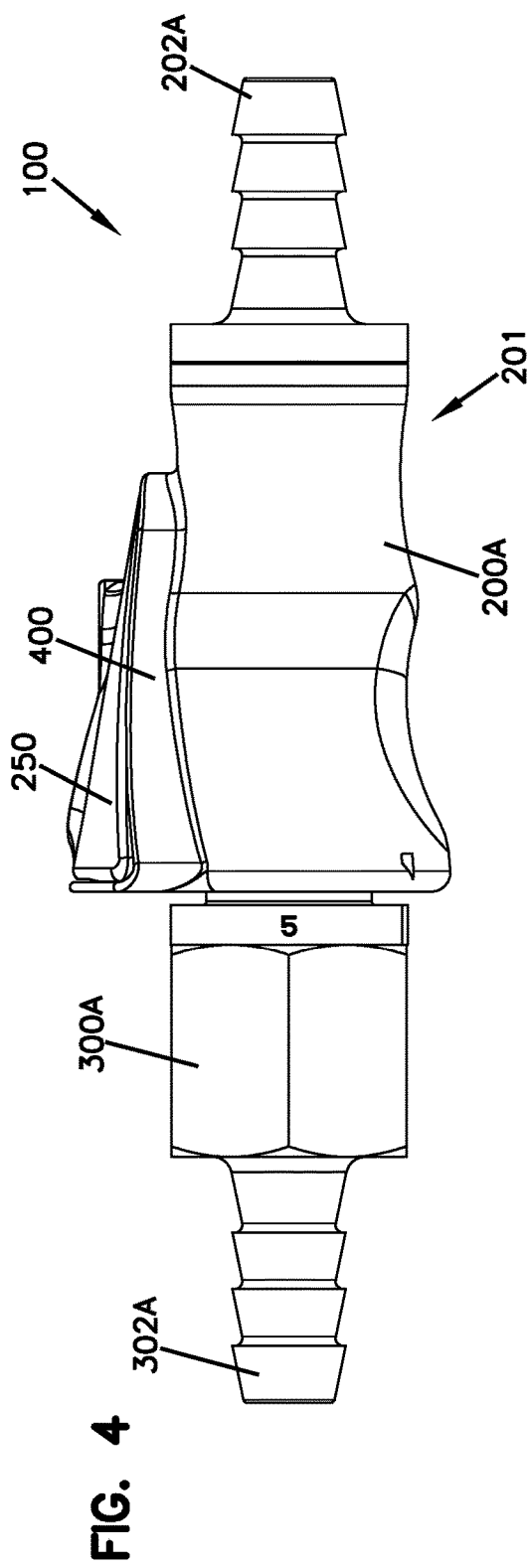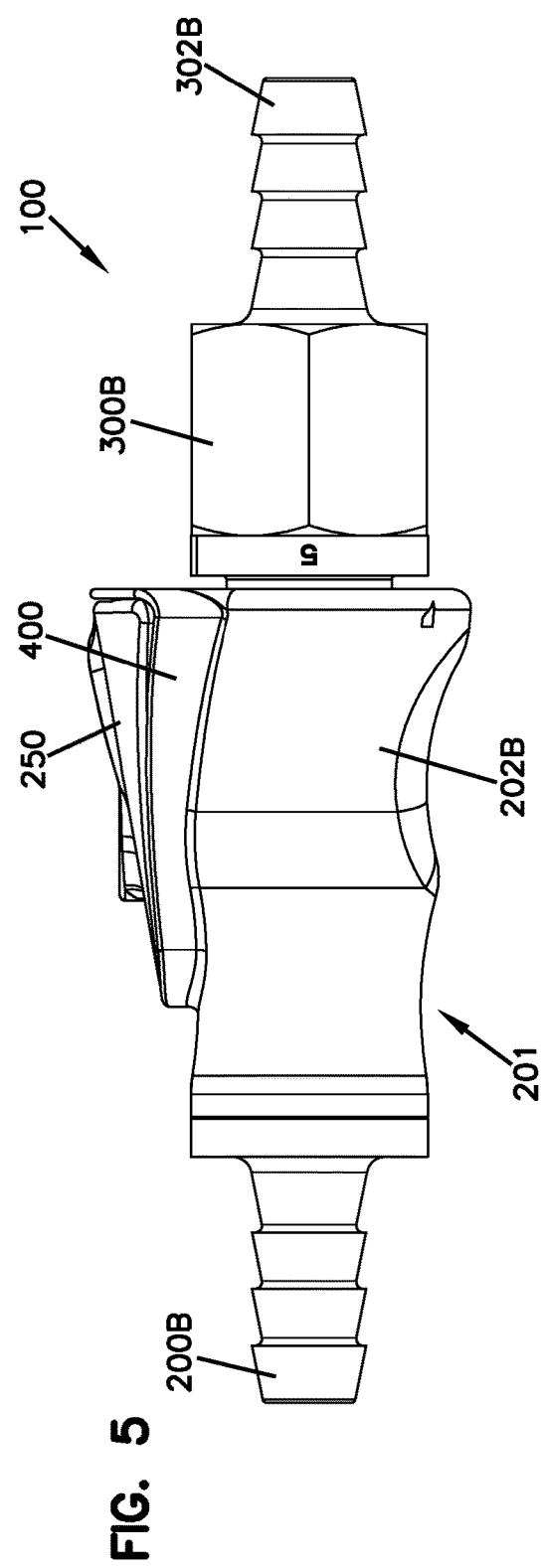

204B

204A

COUPLING ASSEMBLY WITH RETAINING CLIP MEMBER

RELATED APPLICATION(S)

This application is a continuation of U.S. patent application Ser. No. 16/207,787, filed Dec. 3, 2018, which claims priority to U.S. patent application Ser. No. 14/878,464, filed Oct. 8, 2015, which issued as U.S. Pat. No. 10,151,409 and claims priority to U.S. Patent Application Ser. No. 62/061,791, filed on Oct. 9, 2014 and U.S. Patent Application Ser. No. 62/102,841, filed on Jan. 13, 2015, the entireties of which are hereby incorporated by reference.

BACKGROUND

Coupling assemblies typically include female and male coupling devices that are connected to create a fluid flow path therebetween. Such coupling assemblies can be used in various applications to connect sources of fluid with destinations for that fluid.

SUMMARY

In one aspect, a female coupling device includes: a main body defining a first fluid passageway therethrough; and a clip member coupled to the main body, the clip member defining a clip body and a plurality of arms extending perpendicularly therefrom, with the plurality of arms forming at least one pair of arms, with the pair of arms including a first distance therebetween and a second distance therebetween, with the first distance being sized to engage a clip groove of a mating male coupling device, and with the second distance being sized to disengage the mating male coupling device; wherein, in a locked position, the pair of arms is positioned so that the first distance is adjacent to the mating male coupling device so that the pair of arms is received in the clip groove to couple the mating male coupling device to the female coupling device; and wherein, in an unlocked position, the pair of arms is positioned so that the second distance is adjacent to the mating male coupling device to allow the mating male coupling device to be removed from the female coupling device.

In another aspect, a female coupling assembly includes: a main body including a first female coupling device and a second female coupling device, with the first female coupling device defining a first fluid passageway therethrough, and the second female coupling device defining a second fluid passageway therethrough; and a clip member coupled to the main body, the clip member defining a clip body and a plurality of arms extending perpendicularly therefrom, with the plurality of arms forming at least one pair of arms, with the pair of arms including a first distance therebetween and a second distance therebetween, with the first distance being sized to engage a clip groove of a mating male coupling device, and with the second distance being sized to disengage the mating male coupling device; wherein, in a locked position, the pair of arms is positioned so that the first distance is adjacent to the mating male coupling device so that the pair of arms is received in the clip groove to couple the mating male coupling device to the female coupling assembly; and wherein, in an unlocked position, the pair of arms is positioned so that the second distance is adjacent to the mating male coupling device and the pair of arms is flexed outwardly to allow the mating male coupling device to be removed from the female coupling assembly.

In another aspect, a female coupling assembly includes: a main body including a first female coupling device and a second female coupling device, with the first female coupling device defining a first fluid passageway therethrough, and the second female coupling device defining a second fluid passageway therethrough; and a clip member coupled to the main body, the clip member defining a clip body and a plurality of arms extending perpendicularly therefrom, with the plurality of arms forming at least one pair of arms, with the pair of arms including a first distance therebetween and a second distance therebetween, with the first distance being sized to engage a clip groove of a mating male coupling device, and with the second distance being sized to disengage the mating male coupling device; wherein, in a locked position, the pair of arms is positioned so that the first distance is adjacent to the mating male coupling device so that the pair of arms is received in the clip groove to couple the mating male coupling device to the female coupling assembly; and wherein, in an unlocked position, the pair of arms is positioned so that the second distance is adjacent to the mating male coupling device to allow the mating male coupling device to be removed from the female coupling assembly.

DESCRIPTION OF THE DRAWINGS

Reference is now made to the accompanying drawings, which are not necessarily drawn to scale.

FIG. 4 is a side view of the coupling assembly of FIG. 1.

FIG. 5 is another side view of the coupling assembly of FIG. 1.

DETAILED DESCRIPTION

In one aspect, the present disclosure relates to a dual coupling assembly including two female coupling devices. Other configurations are possible. For example, in another aspect, the present disclosure relates to a coupling assembly including a single female coupling device.

Figure 31:
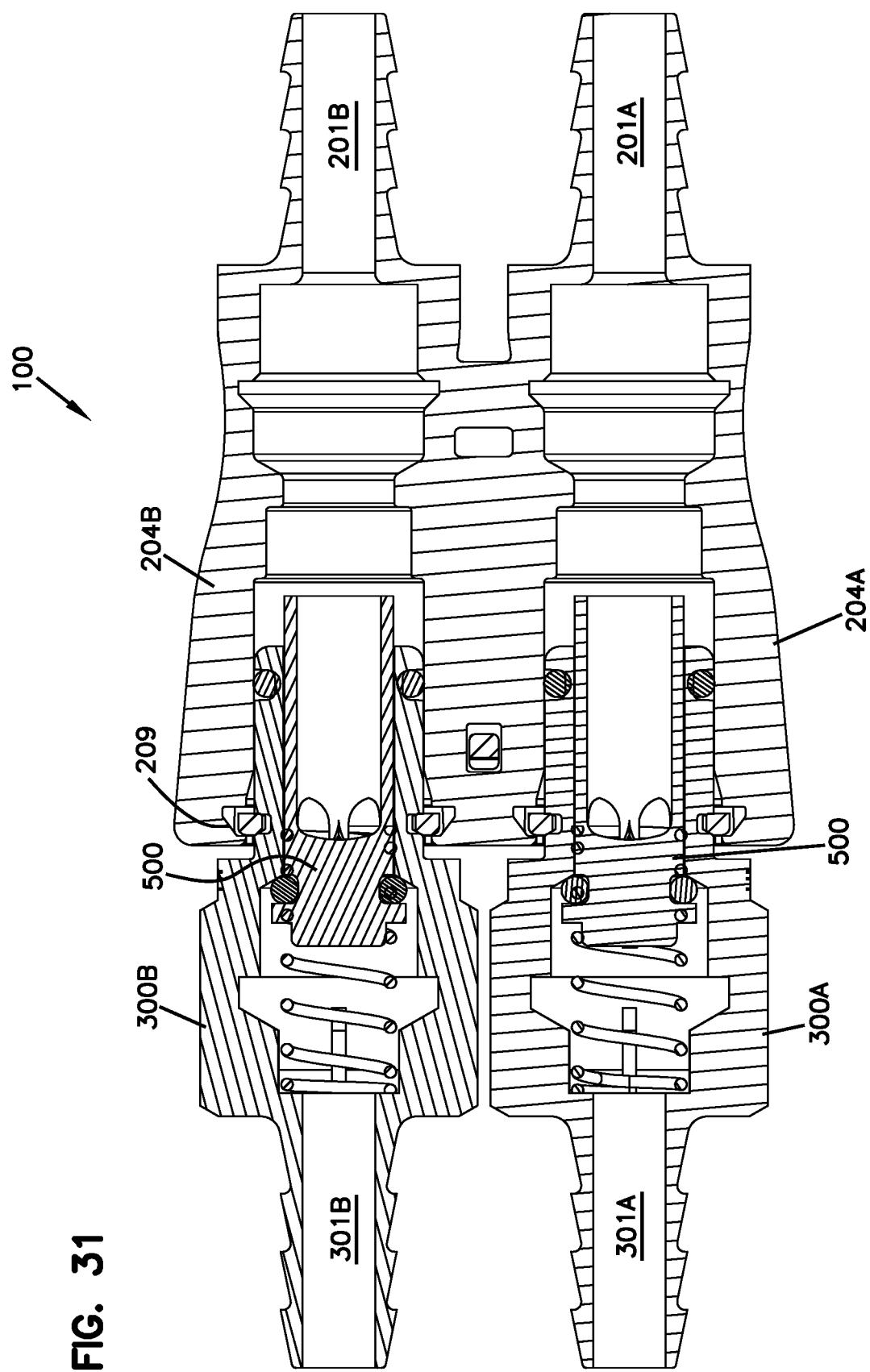
FIG. 31 is a cross-sectional view of the coupling assembly of FIG. 1.
Figure 32:
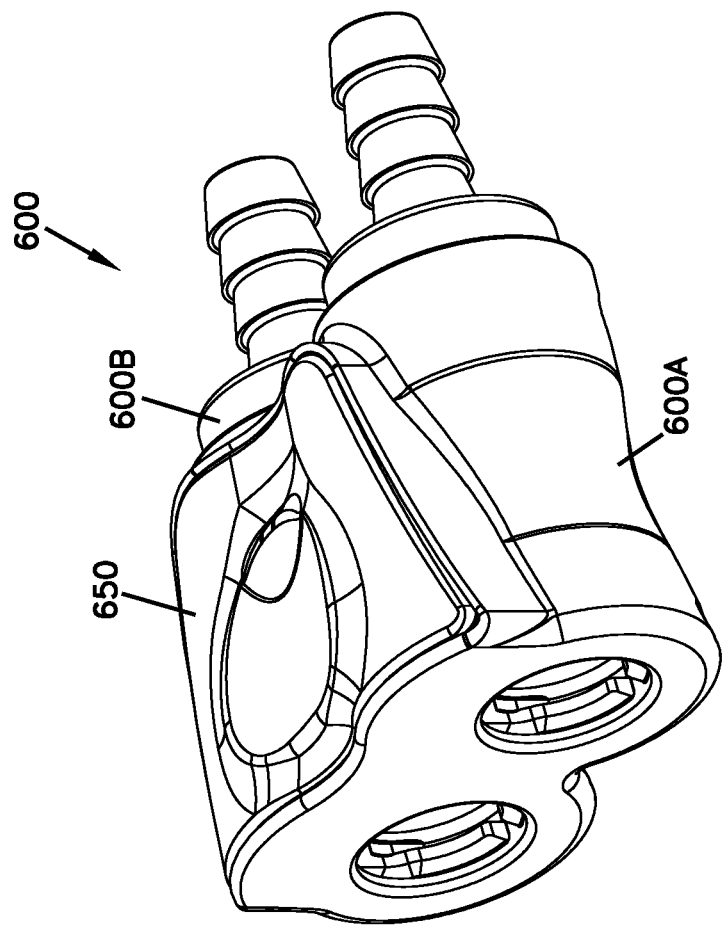
FIG. 32 is a perspective view of another female coupling assembly.
Figure 33:
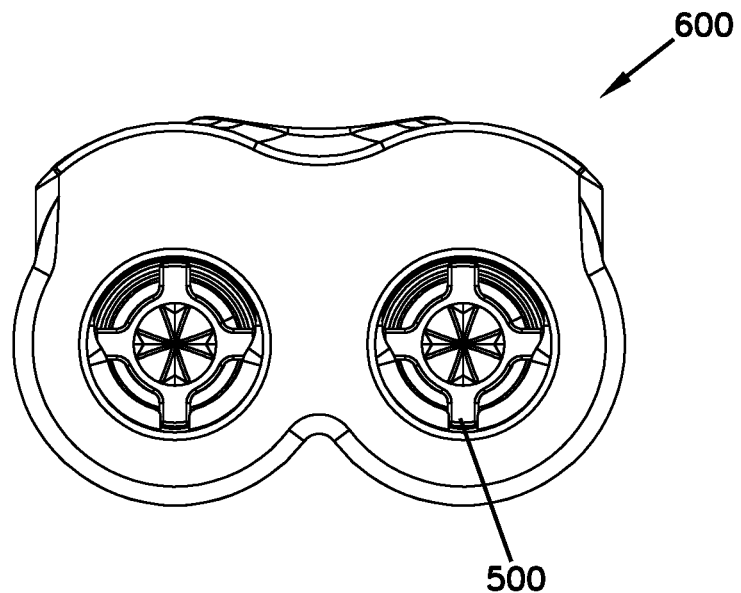
FIG. 33 is an end view of the female coupling assembly of FIG. 32.
Figure 34:
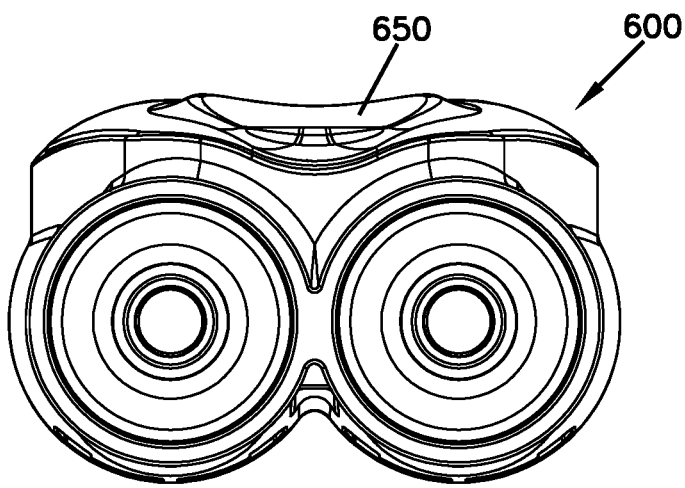
FIG. 34 is an opposite end view of the female coupling assembly of FIG. 32.
Figure 35:
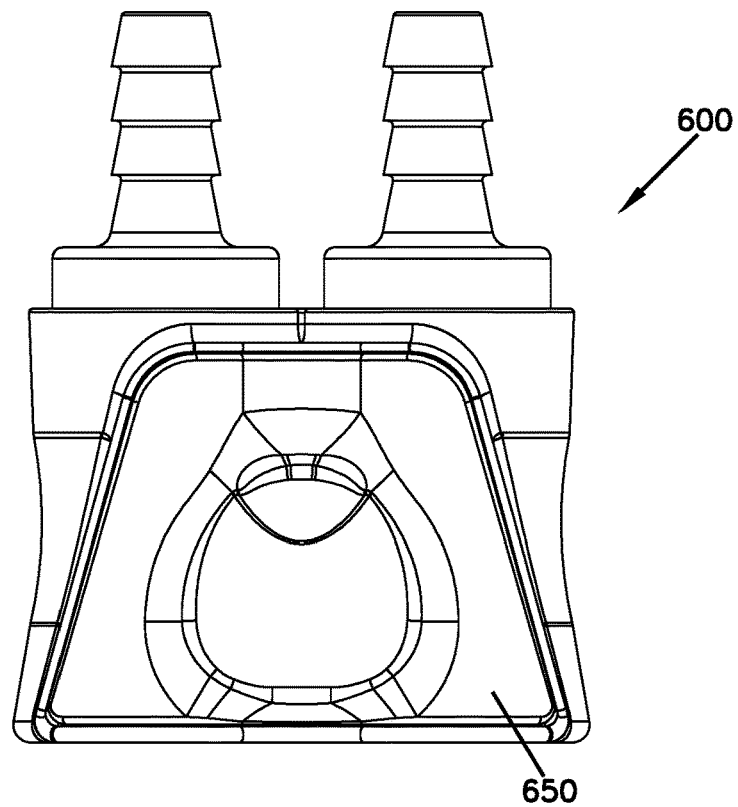
FIG. 35 is a top view of the female coupling assembly of FIG. 32.

In the examples described herein, the coupling assembly is valved (see valving 500 in FIGS. 31 and 33). However, in other examples, the coupling assembly can be non-valved.

Referring now to FIGS. 1-6 and 31, an example coupling assembly 100 is shown. The coupling assembly includes female coupling assembly 201 with female coupling devices 200A, 200B and male coupling devices 300A, 300B.

Referring now to FIGS. 1-20, in this example, the female coupling devices 200A, 200B are joined by a shroud portion 400. The shroud portion 400 is coupled to the female coupling devices 200A, 200B so that the female coupling assembly 201 forms dual, separate fluid passageways. Specifically, each of the female coupling devices 200A, 200B includes a main body 204A, 204B and a termination 202A, 202B. The main body 204A, 204B forms a fluid passageway 201A, 201B therethrough. In these examples, fluid can be any type of fluid, such as a liquid or gas (e.g., air). Each fluid passageway 201A, 201B is separate.

The female coupling assembly 201 can be formed using known techniques, such as sonic welding, staking, press-fitting, threading, insert molding, and/or snapping. In this example, the main bodies 204A, 204B and shroud portion 400 are integrally molded. However, in other examples, the main bodies 204A, 204B, terminations 202A, 202B, and shroud portion 400 can be coupled using sonic welding or other techniques disclosed herein.

The male coupling devices 300A, 300B each includes a main body 304A, 304B and a termination 302A, 302B. The main body 304A, 304B forms a fluid passageway 301A, 301B therethrough and a clip groove 303A, 303B.

The terminations 202A, 202B, 302A, 302B are configured to be coupled to another component, such as fluid lines and/or devices. For example, in one embodiment, the termination 302A is connected to a fluid line extending to a fluid source. The termination 202A is connected to a fluid line extending to a fluid destination. Fluid (i.e., liquid or gas) is provided from the fluid source, through the fluid line, through the female coupling assembly 201, and to the fluid destination. The terminations 302B and 202B can be similarly connected to the same or a different fluid source and destination.

Referring now to FIGS. 21-26, the female coupling assembly 201 includes a clip member 250. The clip member 250 is protected by the shroud portion 400 and moves in directions 254, 255 (see FIGS. 27-30) between locked and unlocked positions.

Figure 1:
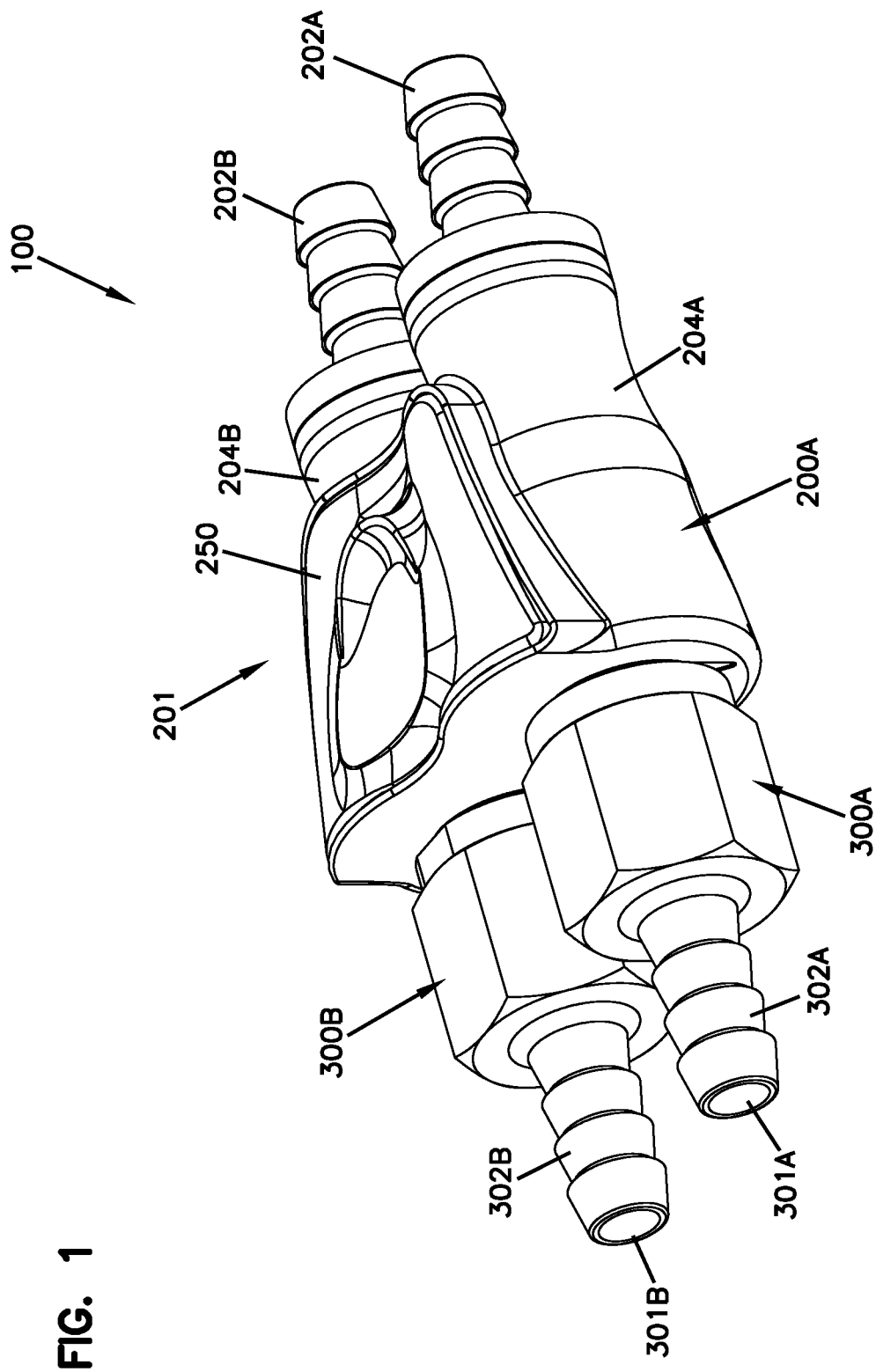
FIG. 1 is a perspective view of an example coupling assembly.
Figure 2:
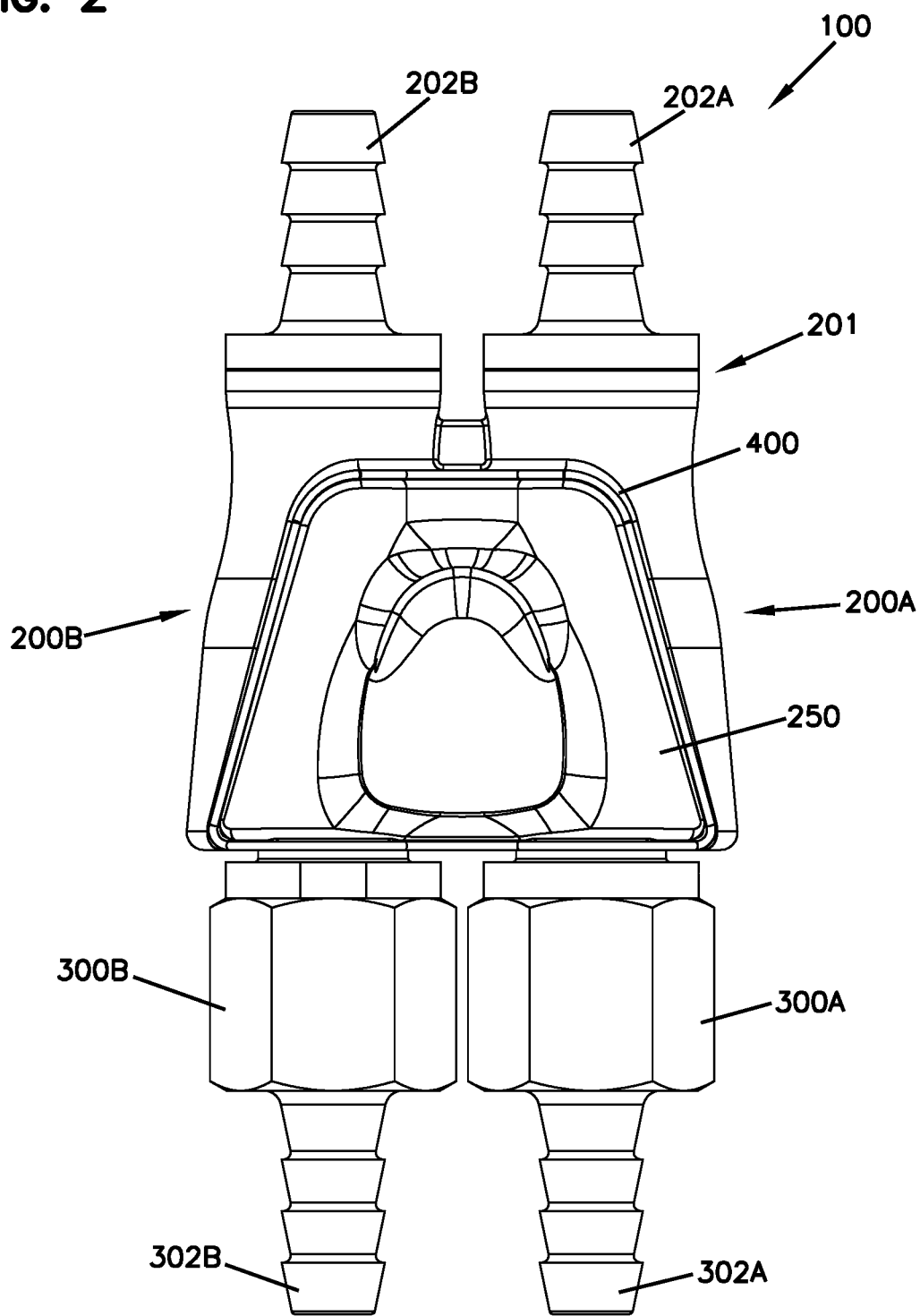
FIG. 2 is a top view of the coupling assembly of FIG. 1.
Figure 3:
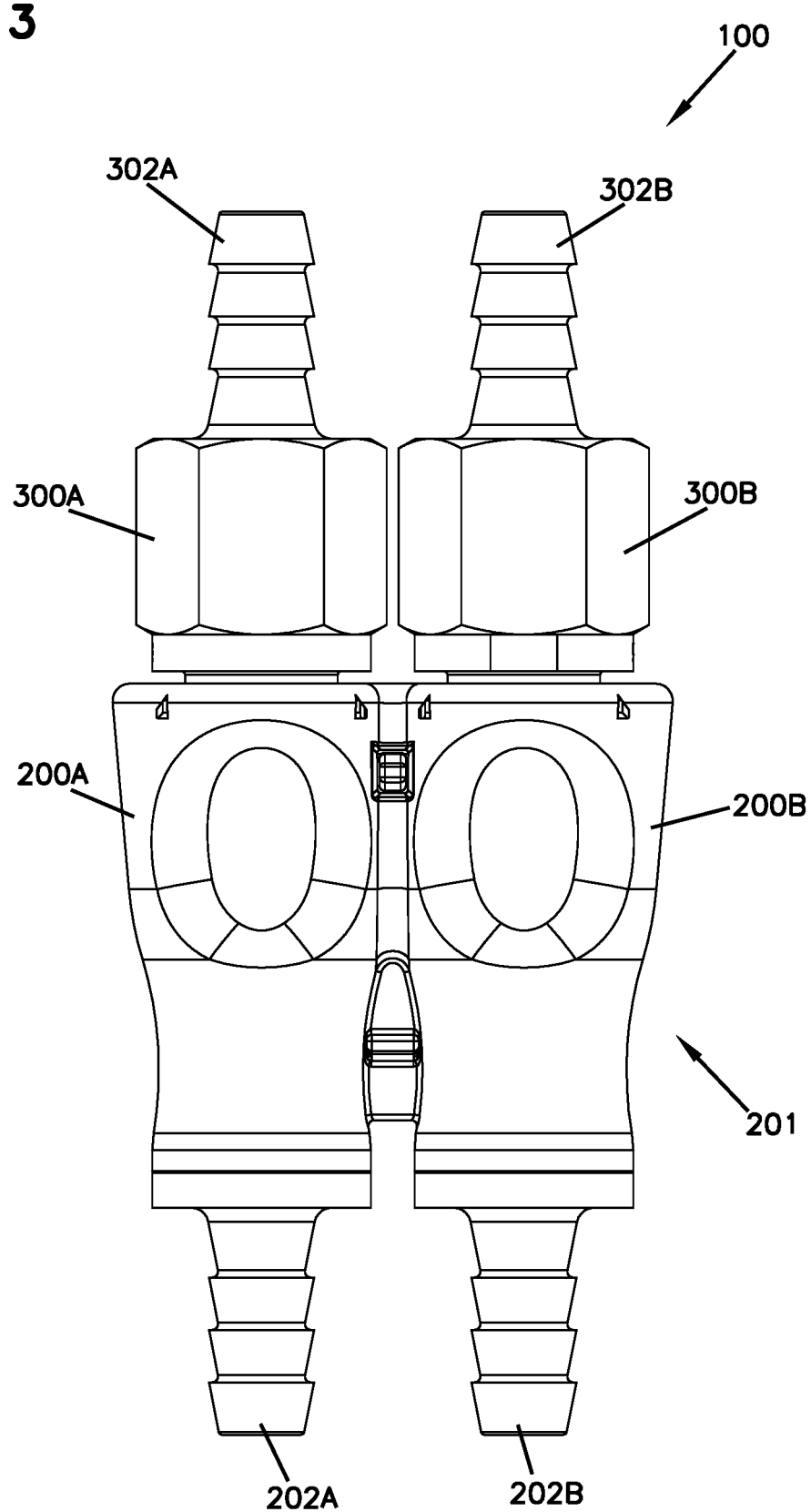
FIG. 3 is a bottom view of the coupling assembly of FIG. 1.
Figure 6:
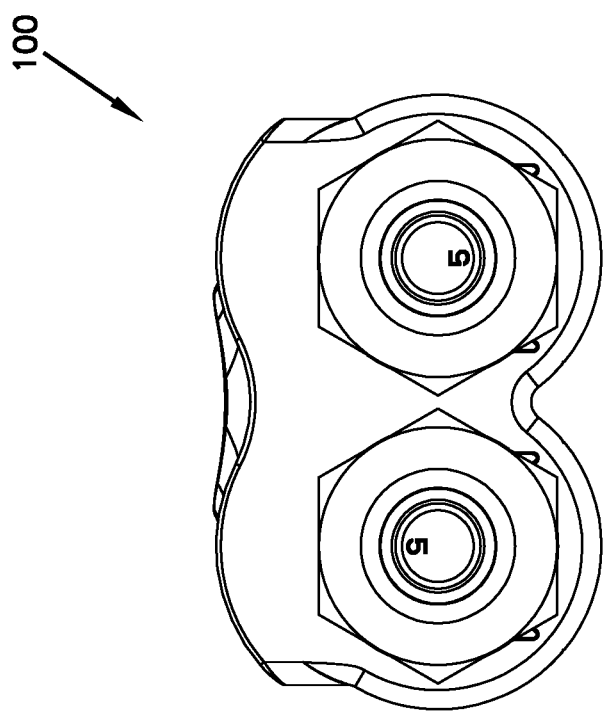
FIG. 6 is an end view of the coupling assembly of FIG. 1.
Figure 7:
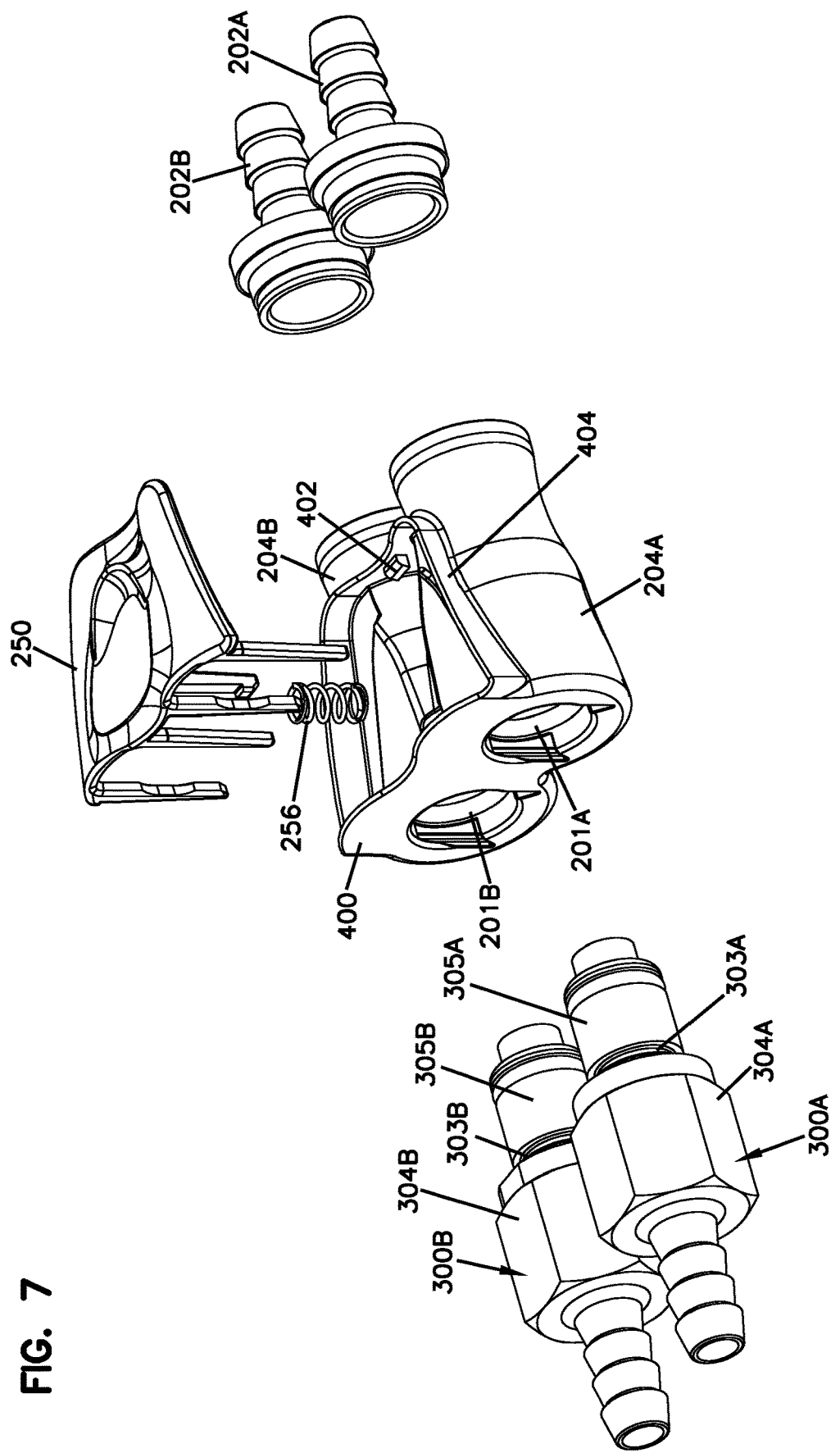
FIG. 7 is a perspective exploded view of the coupling assembly of FIG. 1.
Figure 8:
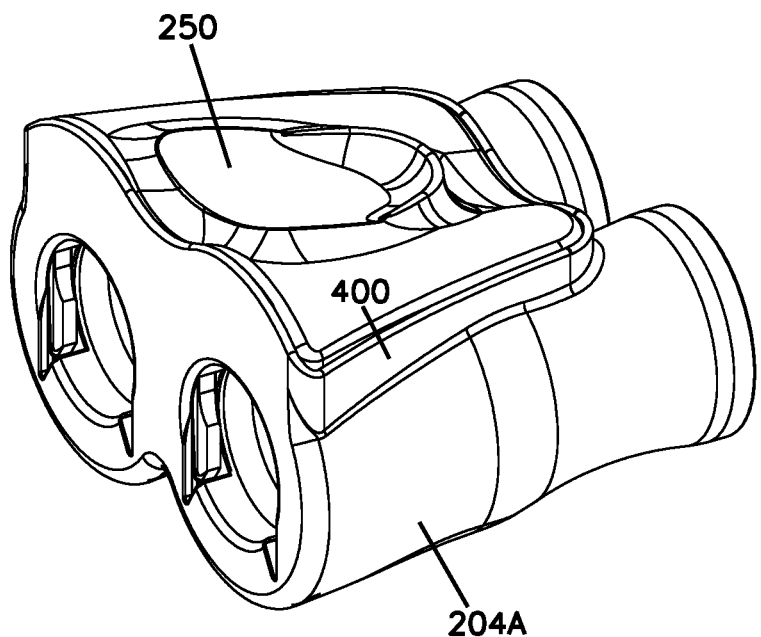
FIG. 8 is a perspective view of a female coupling assembly of the coupling assembly of FIG. 1.
Figure 9:
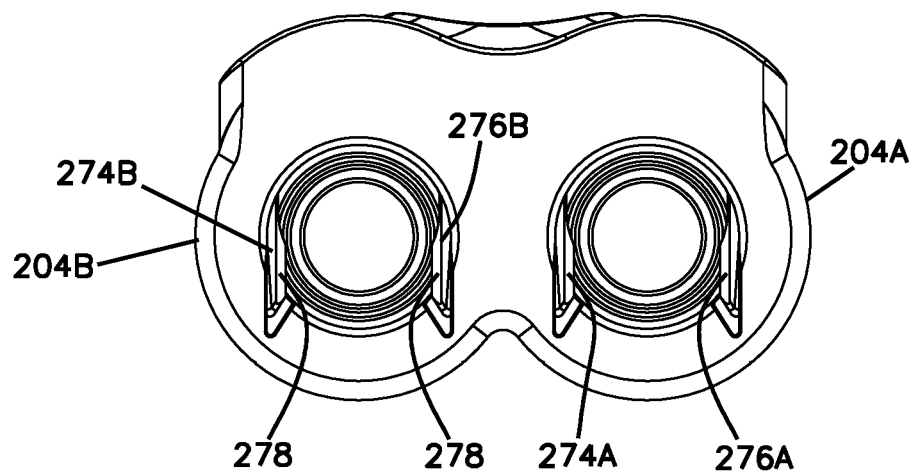
FIG. 9 is an end view of the female coupling assembly of FIG. 8.
Figure 10:
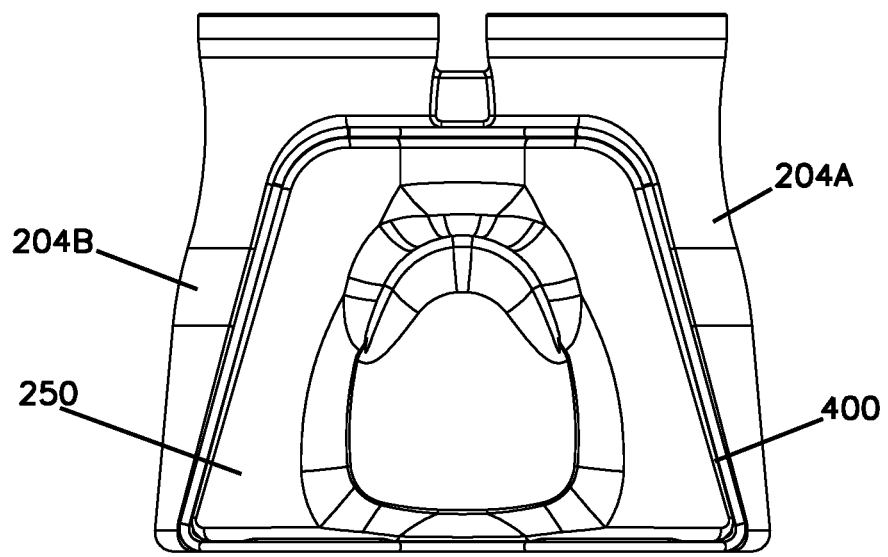
FIG. 10 is a top view of the female coupling assembly of FIG. 8.
Figure 11:
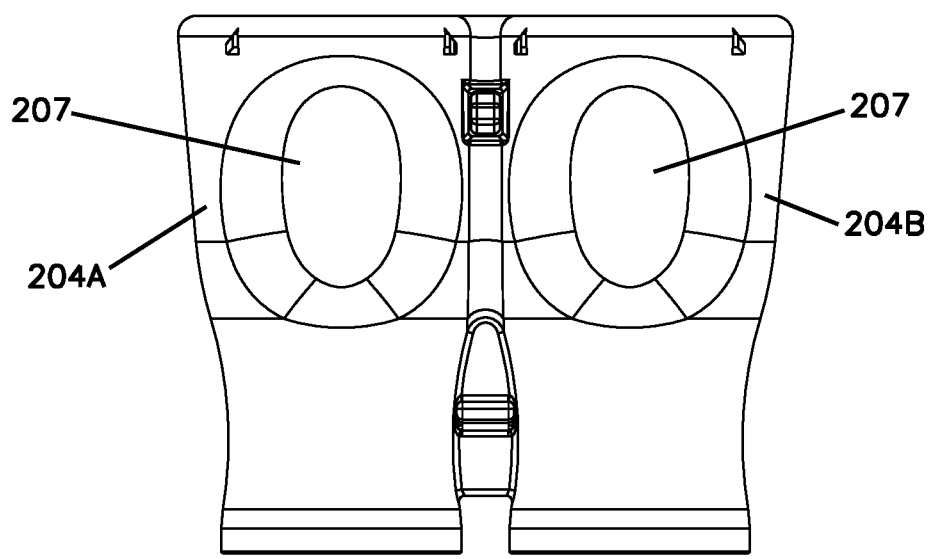
FIG. 11 is a bottom view of the female coupling assembly of FIG. 8.
Figure 12:
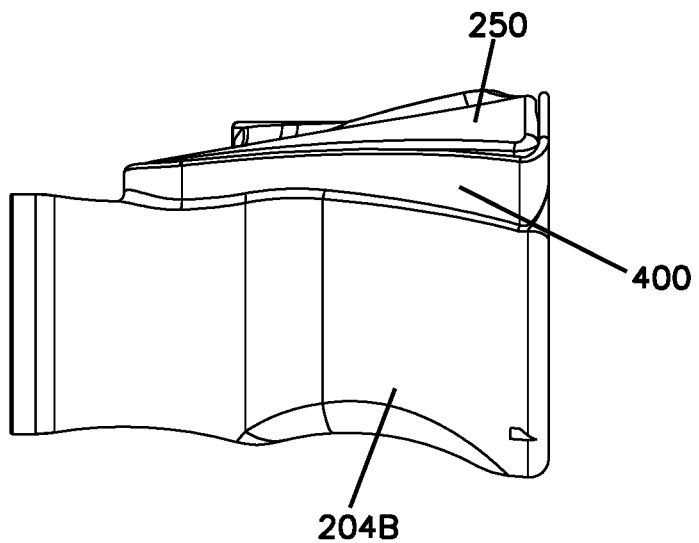
FIG. 12 is a side view of the female coupling assembly of FIG. 8.
Figure 13:
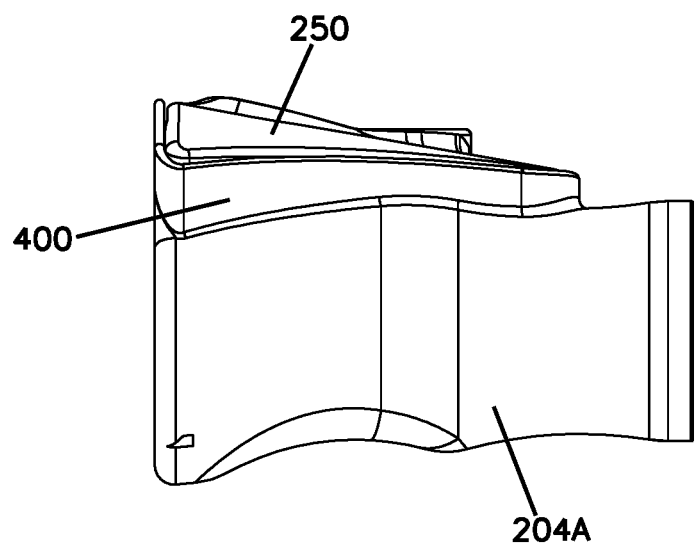
FIG. 13 is another side view of the female coupling assembly of FIG. 8.
Figure 14:
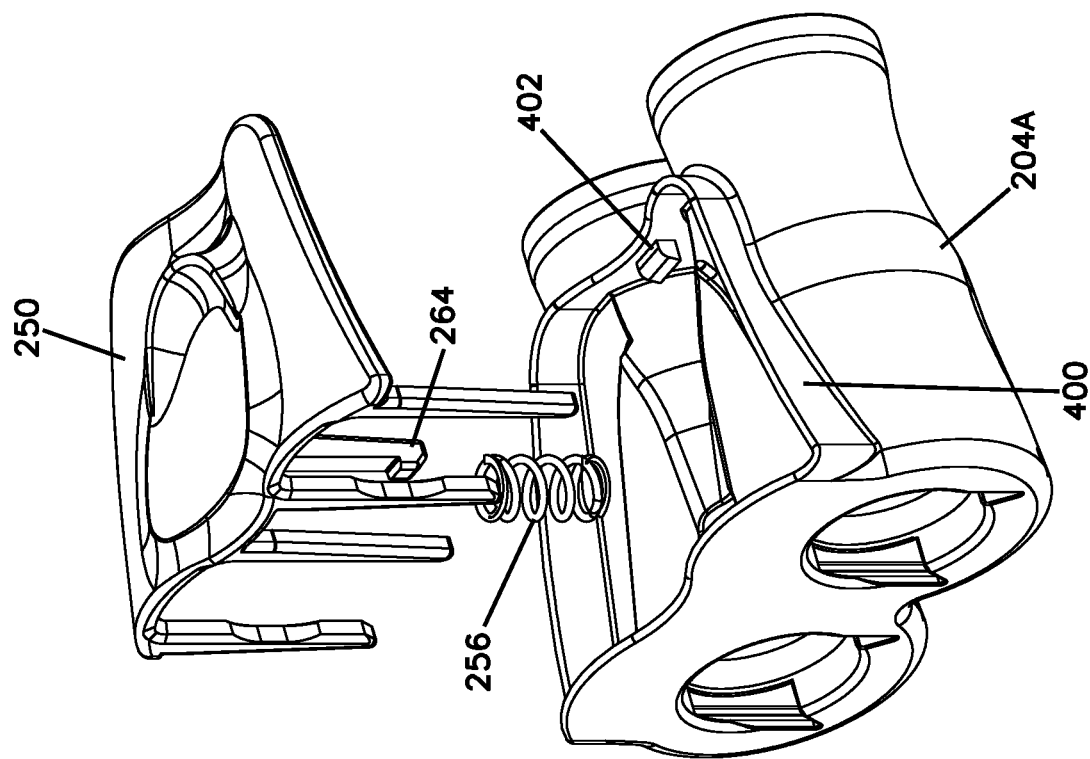
FIG. 14 is an exploded perspective view of the female coupling assembly of FIG. 8.
Figure 15:
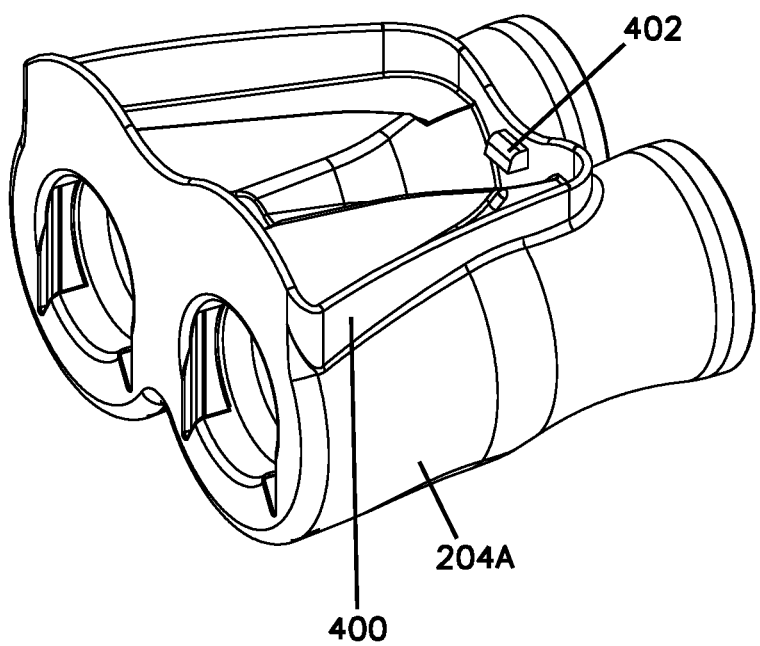
FIG. 15 is a perspective view of the female coupling assembly of FIG. 8 without the clip member.
Figure 16:
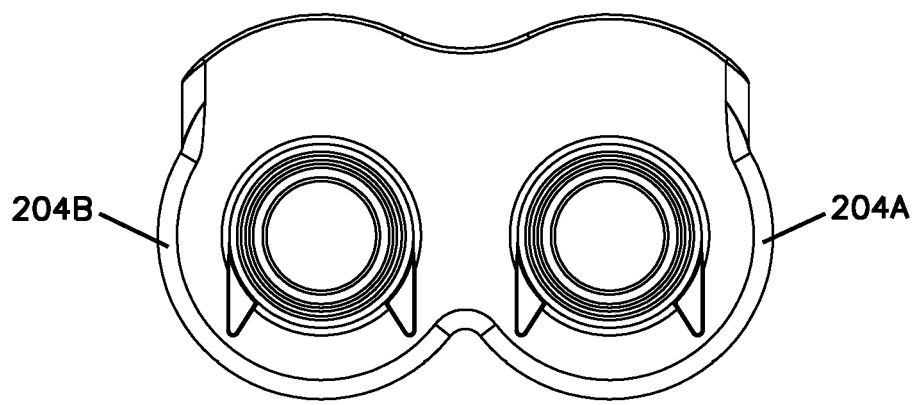
FIG. 16 is an end view of the female coupling assembly of FIG. 15.
Figure 17:
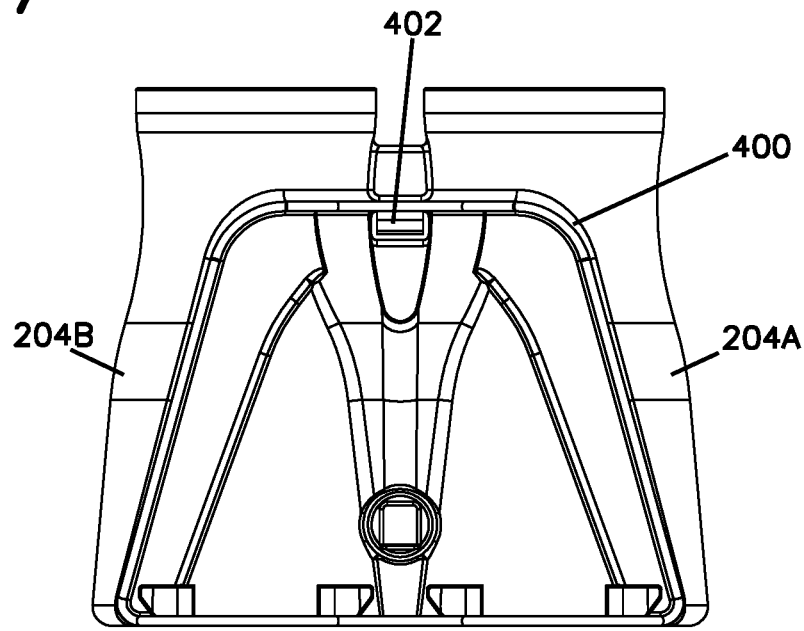
FIG. 17 is a top view of the female coupling assembly of FIG. 15.
Figure 18:
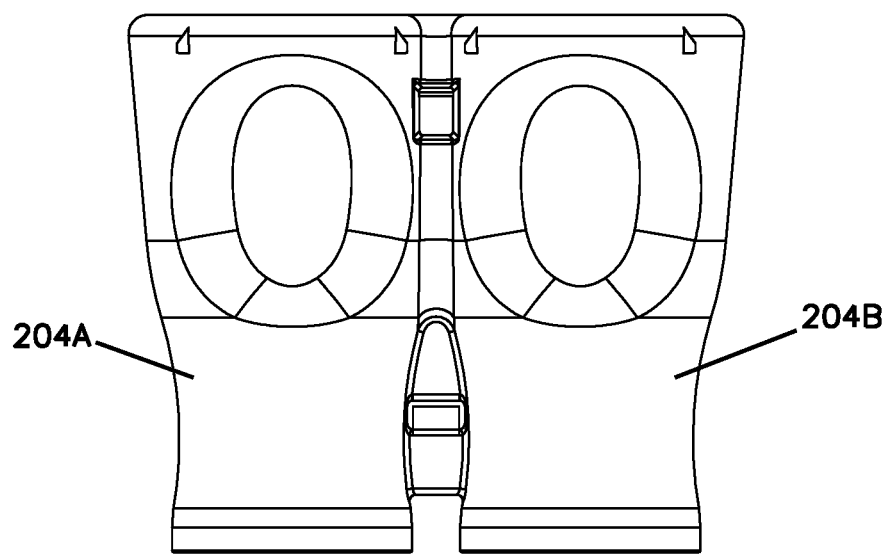
FIG. 18 is a bottom view of the female coupling assembly of FIG. 15.
Figure 19:
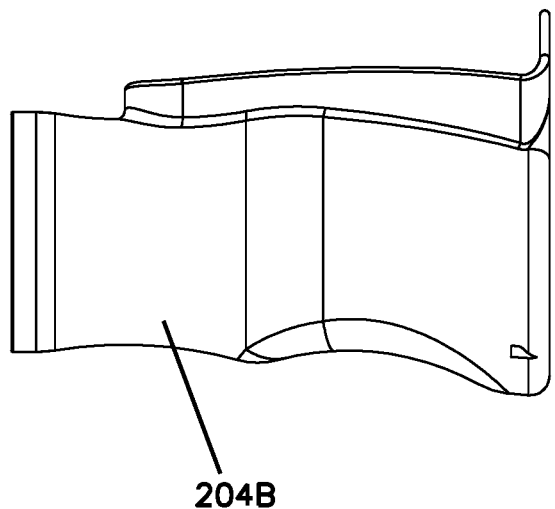
FIG. 19 is a side view of the female coupling assembly of FIG. 15.
Figure 20:
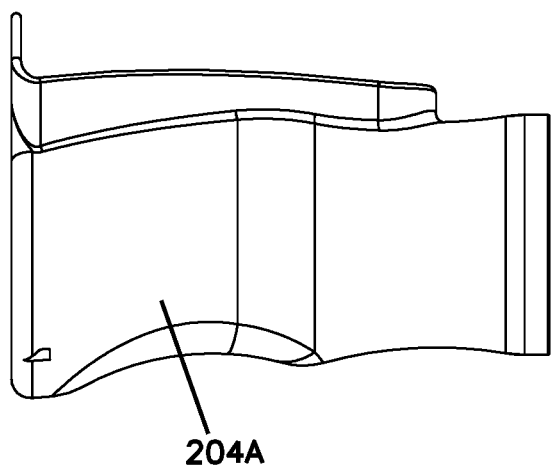
FIG. 20 is another side view of the female coupling assembly of FIG. 15.
Figure 21:
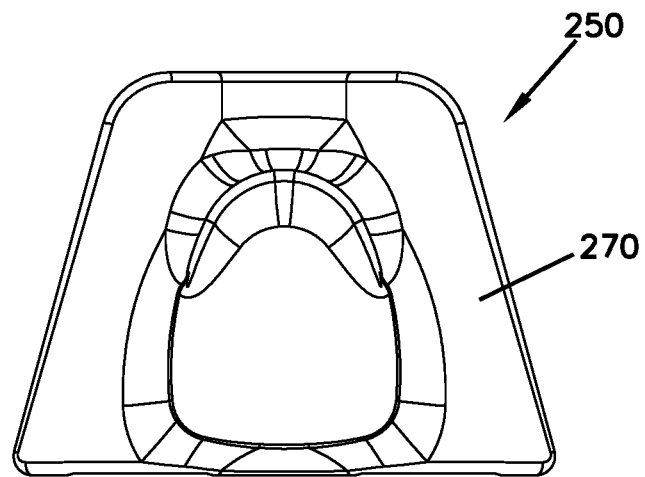
FIG. 21 is a top view of a clip member of the female coupling assembly of FIG. 8.
Figure 22:
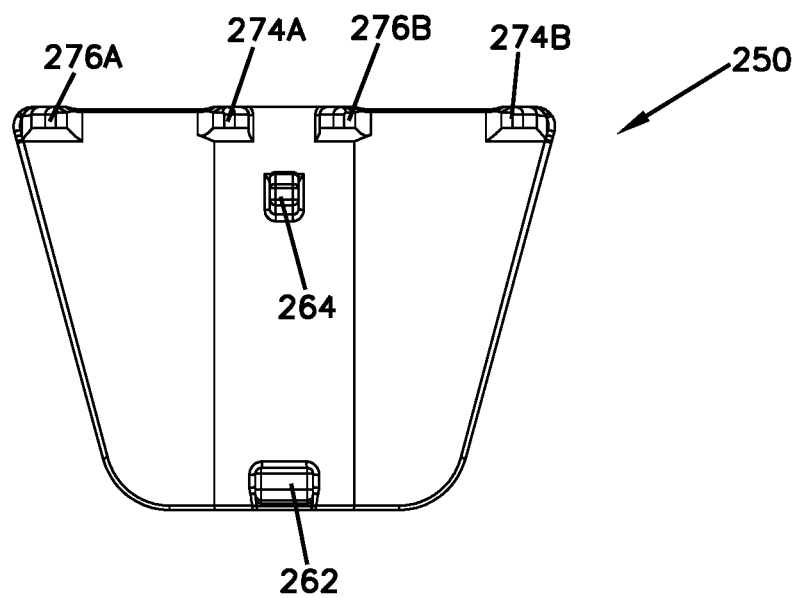
FIG. 22 is a bottom view of the clip member of FIG. 21.
Figure 23:
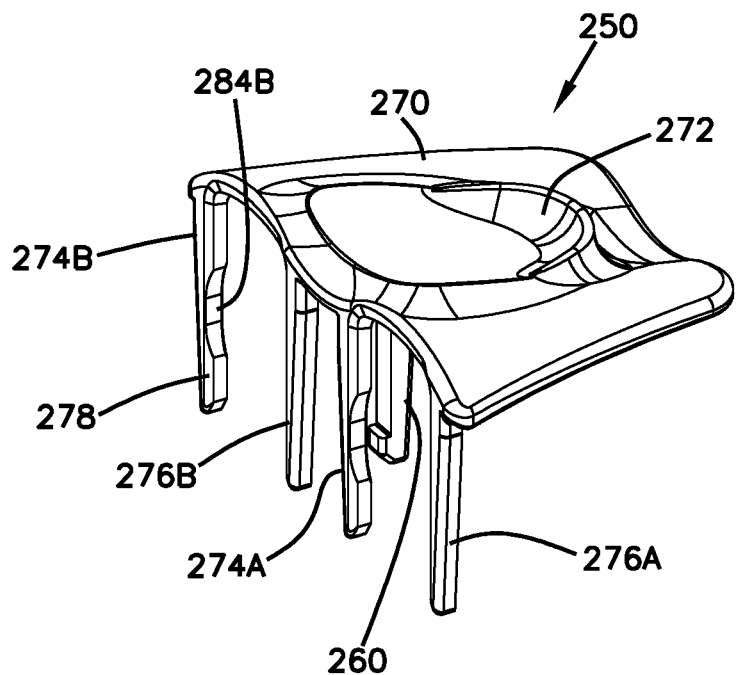
FIG. 23 is a perspective view of the clip member of FIG. 21.
Figure 24:
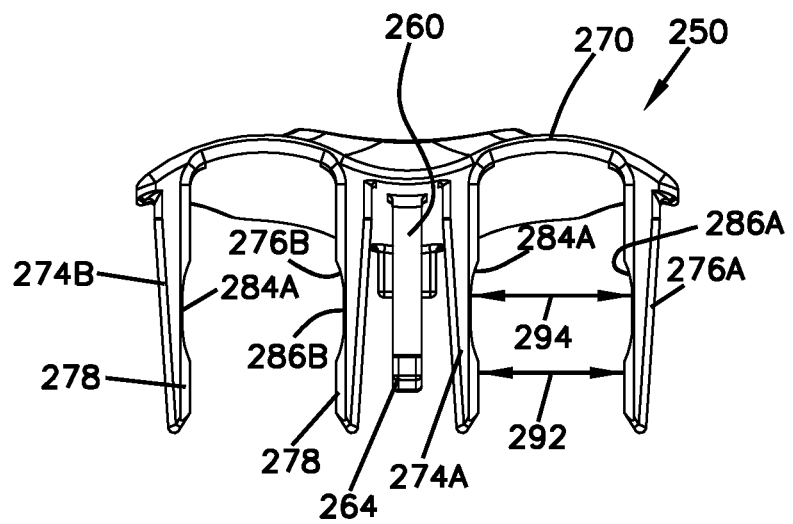
FIG. 24 is an end view of the clip member of FIG. 21.
Figure 25:
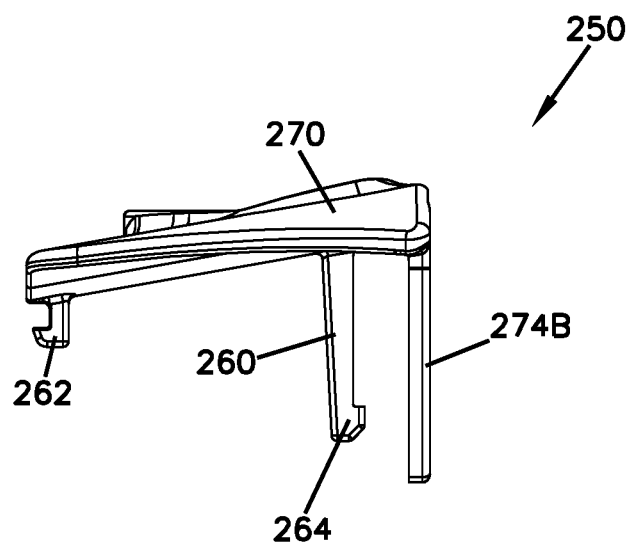
FIG. 25 is a side view of the clip member of FIG. 21.
Figure 26:
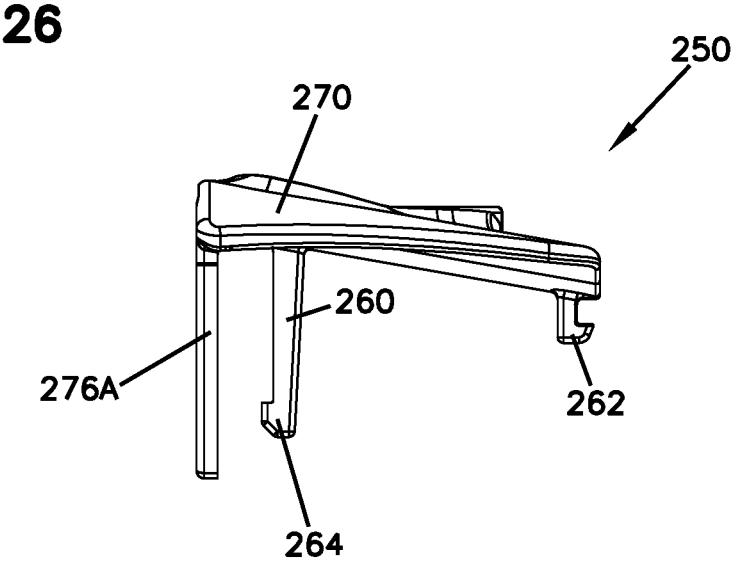
FIG. 26 is another side view of the clip member of FIG. 21.
Figure 27:
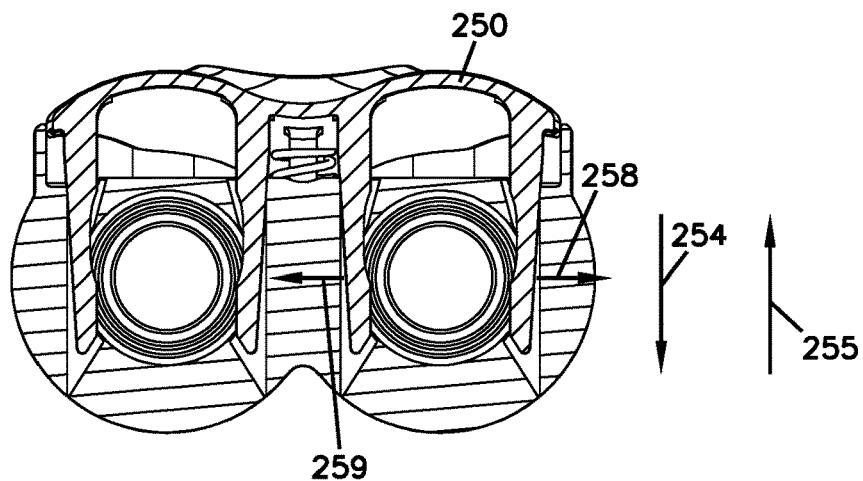
FIG. 27 is a cross-sectional view of the female coupling assembly of FIG. 8 with the clip member in the locked position.
Figure 28:
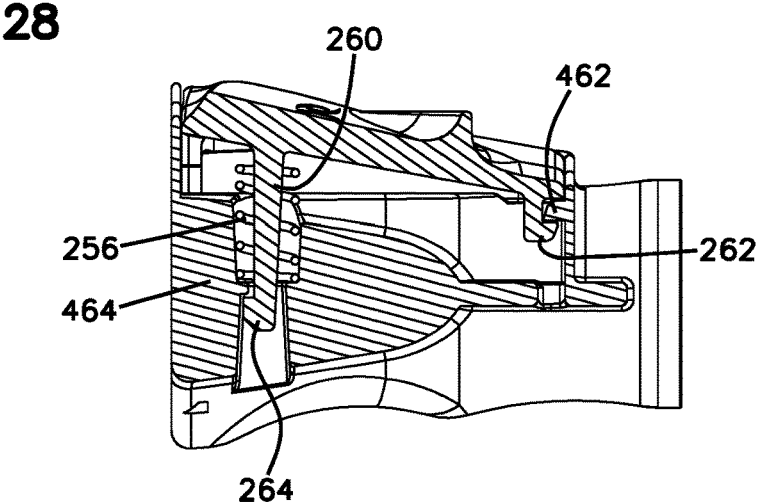
FIG. 28 is another cross-sectional view of the female coupling assembly of FIG. 27.
Figure 29:
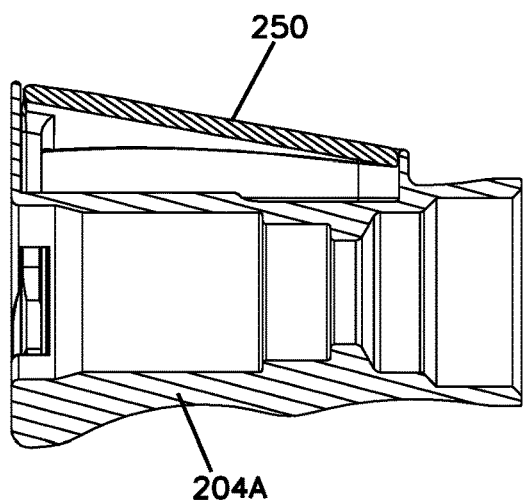
FIG. 29 is another cross-sectional view of the female coupling assembly of FIG. 27.

As shown in FIGS. 27-29, the clip member 250 is in the locked position. A spring 256 forces the clip member 250 in the direction 255 into this locked position. The spring 256 is positioned about a post 260. The clip member 250 is retained in the locked position within the shroud portion 400 by tabs 262, 264 that engage the shroud portion 400. Specifically, the tab 262 engages a tab 462 formed by the shroud portion 400, and the tab 264 on an end of the post 260 engages a tab 464 formed by material extending between the main bodies 204A, 204B to hold the clip member 250 in place.

The clip member 250 includes a main body 270 with a contoured portion 272 that allows for placement of an individual's finger (e.g., thumb) for actuation from the locked state to the unlocked state, as described below. In addition, there are recessed contours 207 formed on the bottom sides of the main bodies 204A, 204B to help locate opposing fingers of the individual to assist in generating the force necessary to actuate the clip member 250. Arms 274A, 274B and 276A, 276B extend generally perpendicularly from the main body 270 in pairs. The arms 274A, 276A form a first pair and are positioned to engage the male coupling device 300A in the clip groove 303A formed on the main body 304A, and the arms 274B, 276B form a second pair and are positioned to engage the male coupling device 300B in the clip groove 303B formed on the main body 304B.

For example, a distance 292 between the arms 274A, 276A is smaller than a diameter of a front portion 305A of the main body 304A of the male coupling device 300A. When the front portion 305A is introduced into the fluid passageway 201A of the female coupling device 200A with the clip member 250 in the locked position, the arms 274A, 274B bend in opposite directions 258, 259 to allow the front portion 305A to pass therethrough. A tapered portion 278 of each arm 274A, 276A facilitates the arms 274A, 276A riding along the front portion 305A as the arms 274A, 276A are forced to bend in directions 258, 259.

When the male coupling device 300A is fully inserted, the arms 274A, 276A are received in the clip groove 303A. Since the clip groove 303A has a smaller diameter, the arms 274A, 276A return to their resting positions within the clip groove 303A. In this configuration, the arms 274A, 276A are positioned in the clip groove 303A at opposite sides of the male coupling device 300A and resist movement of the male coupling device 300A in a direction out of the female coupling device 200A. This retains the male coupling device 300A within the female coupling device 200A so that fluid can flow therethrough.

In this example, the openings formed by the main body 204B each includes an angled front surface 209. See FIG. 31. This angled front surface 209 functions to force the arms 274A, 274B and 276A, 276B inward towards the clip grooves 303A, 303B when the clip member 250 is in the locked position and an axial load is placed on the mating male coupling device 300A, 300B in a direction out of the mating female coupling device 200A, 200B. In this manner, the angled front surfaces 209 help to retain the male coupling device 300A, 300B within the respective female coupling device 200A, 200B.

The male coupling device 300B can be coupled to the main body 204B in a similar manner. Each of the male coupling devices 300A, 300B can be connected separately to the female coupling assembly 201 without impacting the connection state of the other coupling device 300A, 300B. In other words, since the clip member 250 remains in the locked position during insertion of the male coupling devices 300A, 300B, the introduction of a second male coupling device while a first male coupling device is already connected does not disconnect the first male coupling device.

When the clip member 250 is depressed in the direction 254 against the spring 256, any of the male coupling devices 300A, 300B that are coupled to the female coupling assembly 201 can be disconnected from the female coupling assembly 201.

Figure 30:
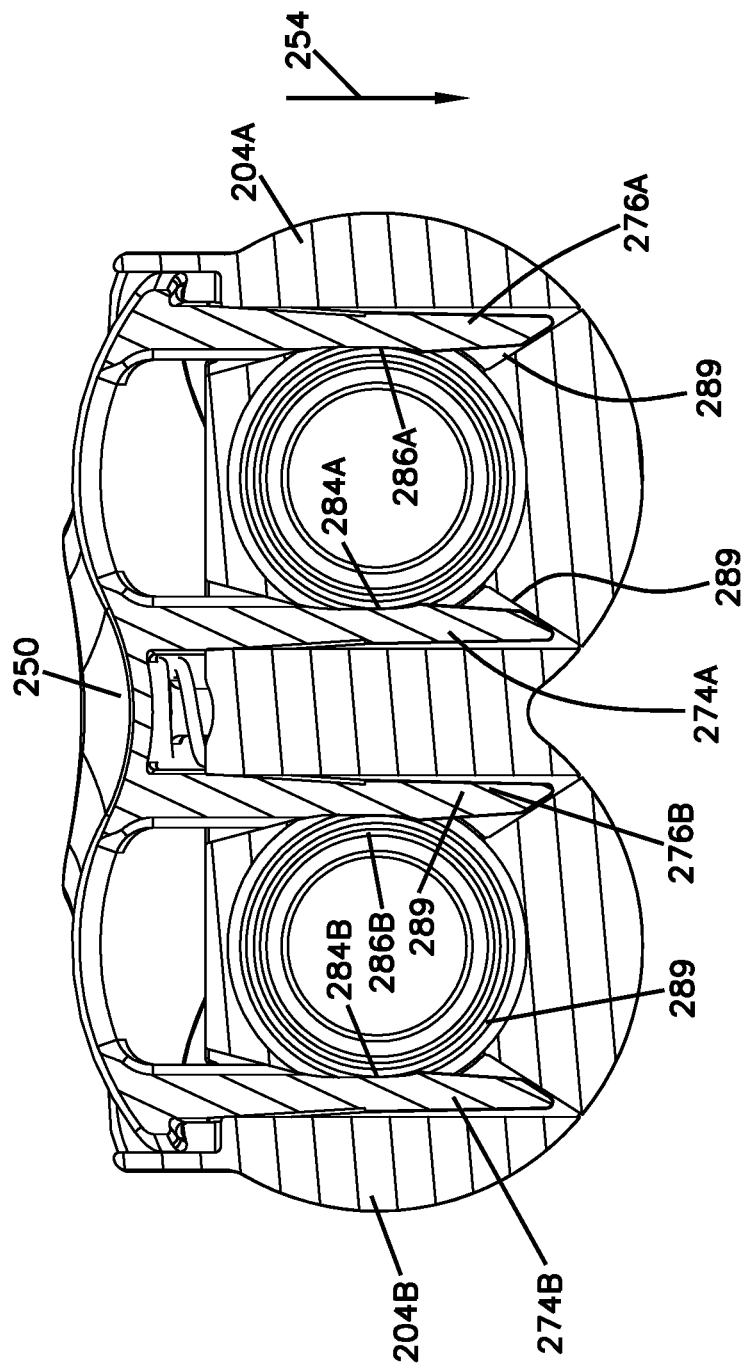
FIG. 30 is a cross-sectional view of the female coupling assembly of FIG. 8 with the clip member in the unlocked position.

The unlocked position for the clip member 250 is shown in FIG. 30. When depressed, the arms 274A, 276A (and 274B, 276B) are moved so that notches 284A, 286A, are positioned at the clip groove 303A. In addition, ends of the arms 274A, 276A contact angled surfaces 289 formed by the main body 204A to cause the arms 274A, 276A to move in the directions 258, 259. This allows the front portion 305A to clear the arms 274A, 276A and thereupon remove the male coupling device 300A from the female coupling device 200A. In other words, since the distance 294 at the notches 284A, 286A is larger (i.e., wider) than the distance 292, the arms 274A, 276A can clear the clip groove 303A and front portion 305A to allow for removal of the male coupling device 300A. Removal of the male coupling device 300B can be accomplished in a similar manner.

When the clip member 250 is released, the spring 256 thereupon moves the clip member 250 in the direction 255 back into the locked position.

In example embodiments, the female coupling assembly 201 is formed using various polymeric materials. In one example, the main bodies 204A, 204B (including terminations 202A, 202B) and shroud portion 400 are made of ABS (Acrylonitrile butadiene styrene), and clip member 250 is made of acetal. These structures can be formed using various techniques, such as injected molding. Other materials, such as polycarbonate, polysulfone, nylon, and polypropylene, can be used.

Referring now to FIGS. 32-49, another example female coupling assembly 600 is shown. The female coupling assembly 600 is similar to the female coupling assembly 201 described above except for the noted differences below.

The female coupling assembly 600 includes female coupling devices 600A, 600B and a clip member 650. The female coupling devices 600A, 600B include valves 500.

As shown in FIGS. 44-49, the clip member 650 includes a main body 670 with arms 674A, 674B and 676A, 676B extend generally perpendicularly from the main body 670 in pairs like clip member 250 described herein.

Each of the arms 672A, 674A, 672B, 674B includes a bottom portion 672A, 674A, 672B, 674B that extends from the arms 674A, 674B and 676A, 676B, respectively. Each pair of the bottom portions 672A, 674A, 672B, 674B extends towards the opposite bottom portion 672A, 674A, 672B, 674B, respectively. Each of the bottom portions 672A, 674A, 672B, 674B includes a contoured section 678 sized to be received in the clip groove of a mating male coupling device, as described below. The section 678 also assists in the deflection of the arms 674A, 674B and 676A, 676B during connection of the male coupling device 300A.

Each pair of the bottom portions 672A, 674A, 672B, 674B forms an opening 676 therebetween, so that the bottom portions 672A, 674A, 672B, 674B do not extend completely to touch. The opening 676 allows the respective arms 674A, 674B and 676A, 676B to flex during insertion of the male coupling device, so that the arms 674A, 674B and 676A, 676B and bottom portions 672A, 674A, 672B, 674B move outwardly to allow for insertion of the male coupling device 300A.

When the male coupling device 300A is fully inserted into the female coupling device 600A of the female coupling assembly 600, the arms 674A, 676A are received in the clip groove 303A. In addition, the bottom portions 672A, 674A are received in the clip groove 303A. Since the clip groove 303A has a smaller diameter, the arms 674A, 676A return to their resting positions within the clip groove 303A. In this configuration, the arms 674A, 676A are positioned in the clip groove 303A at opposite sides of the male coupling device 300A and the bottom portions 672A, 674A at the bottom of the clip groove 303A to resist movement of the male coupling device 300A in a direction out of the female coupling device 600A. This retains the male coupling device 300A within the female coupling device 600A so that fluid can flow therethrough.

Each of the male coupling devices 300A, 300B can be connected separately to the female coupling assembly 600 without impacting the connection state of the other coupling device 300A, 300B. In other words, since the clip member 650 remains in the locked position during insertion of the male coupling devices 300A, 300B, the introduction of a second male coupling device while a first male coupling device is already connected does not disconnect the first male coupling device.

Figure 36:
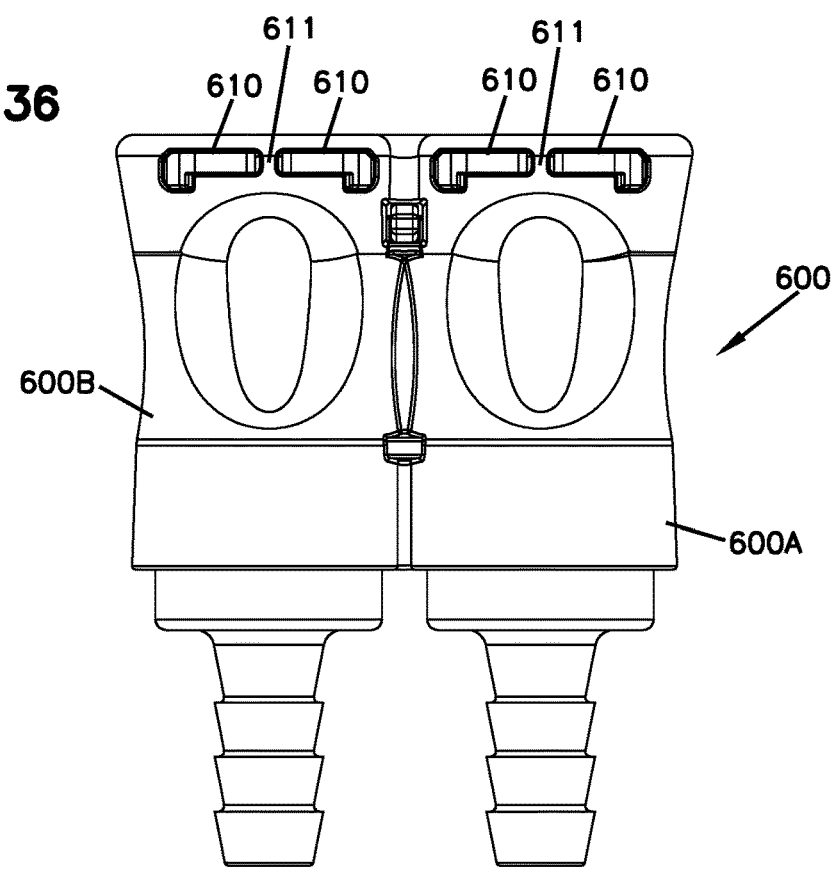
FIG. 36 is a bottom view of the female coupling assembly of FIG. 32.
Figure 37:
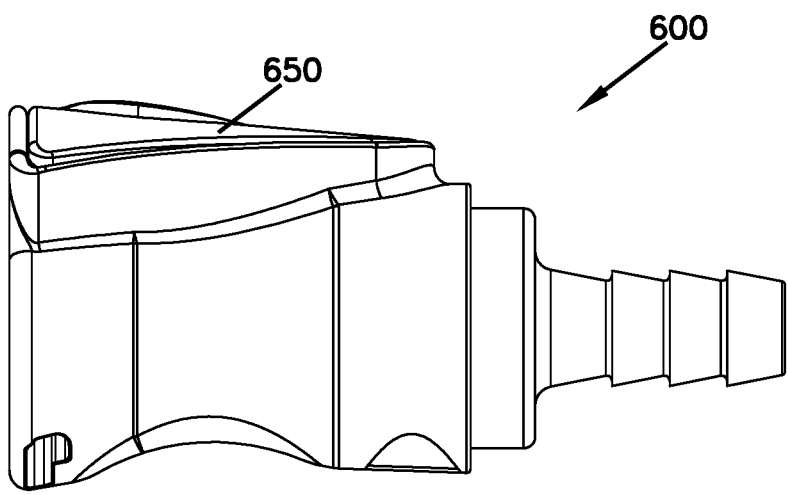
FIG. 37 is a side view of the female coupling assembly of FIG. 32.
Figure 38:
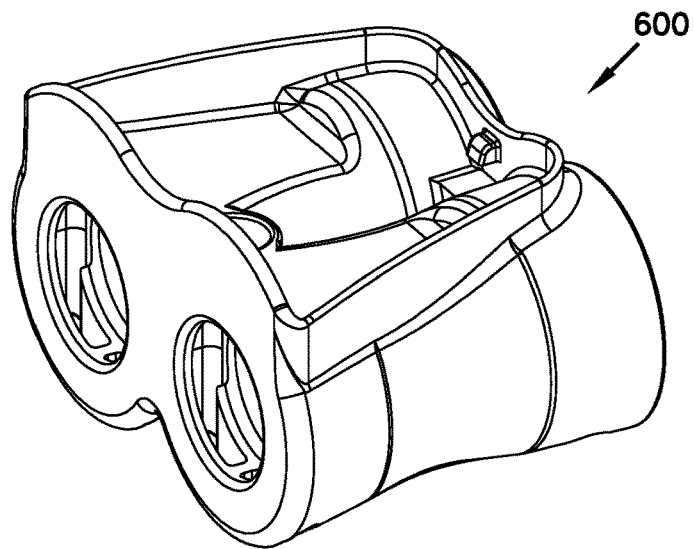
FIG. 38 is a perspective view of the female coupling assembly of FIG. 32 without the clip member.
Figure 39:
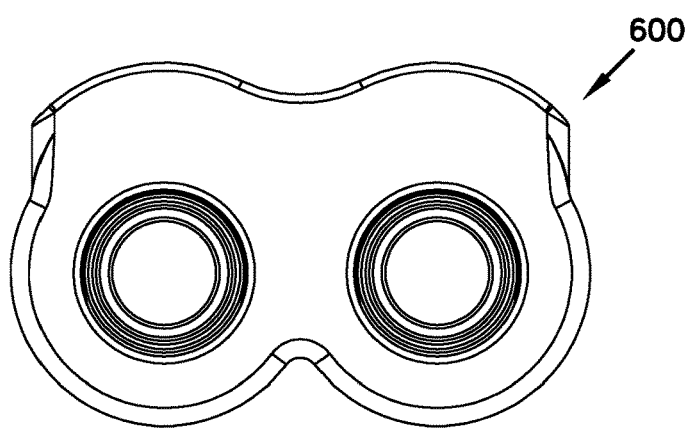
FIG. 39 is an end view of the female coupling assembly of FIG. 38.
Figure 40:
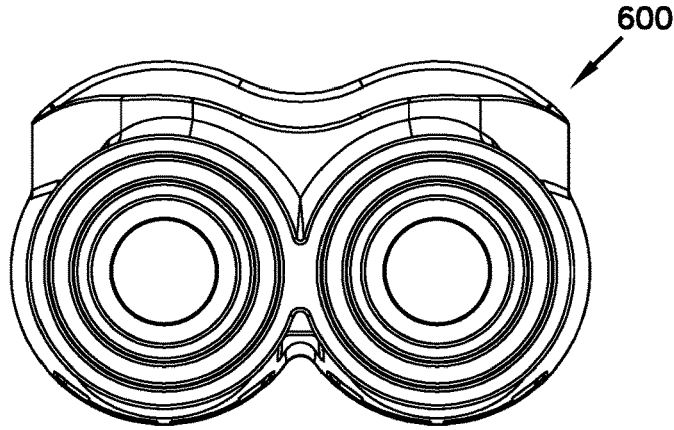
FIG. 40 is an opposite end view of the female coupling assembly of FIG. 38.
Figure 41:
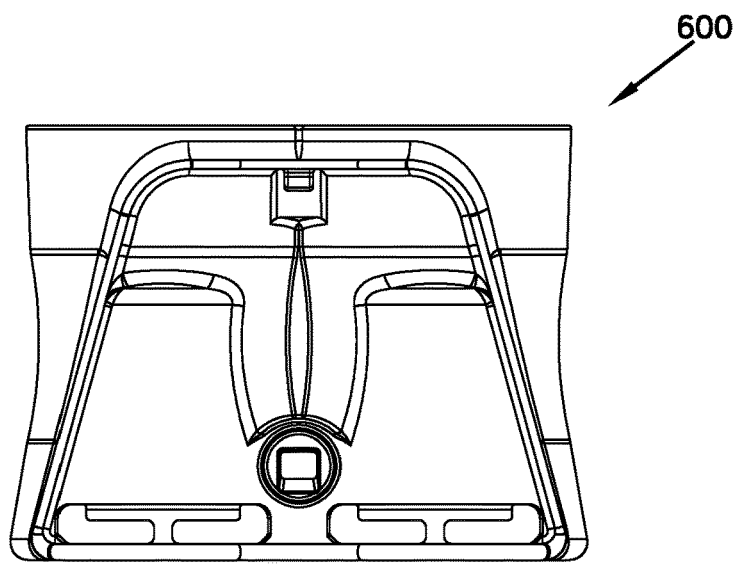
FIG. 41 is a top view of the female coupling assembly of FIG. 38.
Figure 42:
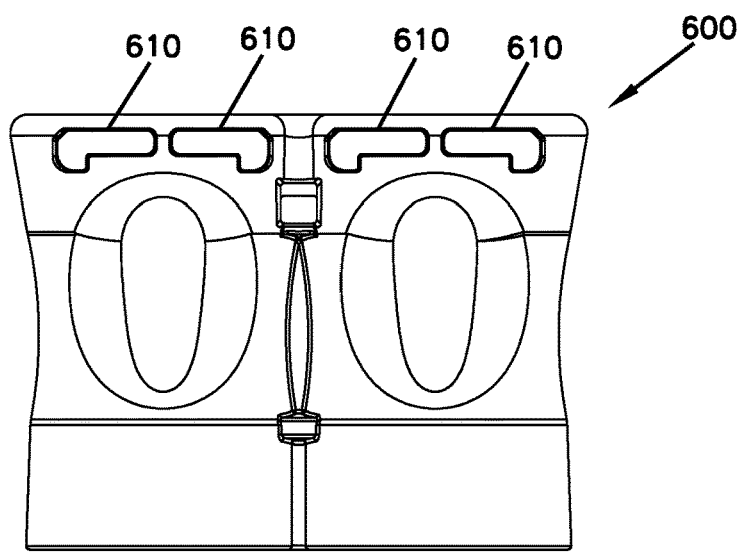
FIG. 42 is a bottom view of the female coupling assembly of FIG. 38.
Figure 43:
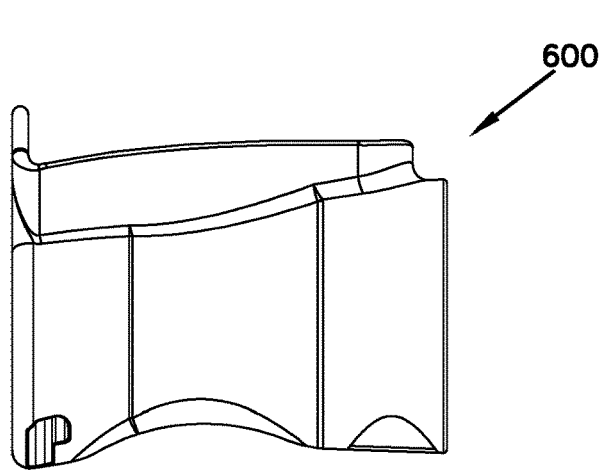
FIG. 43 is a side view of the female coupling assembly of FIG. 38.
Figure 44:
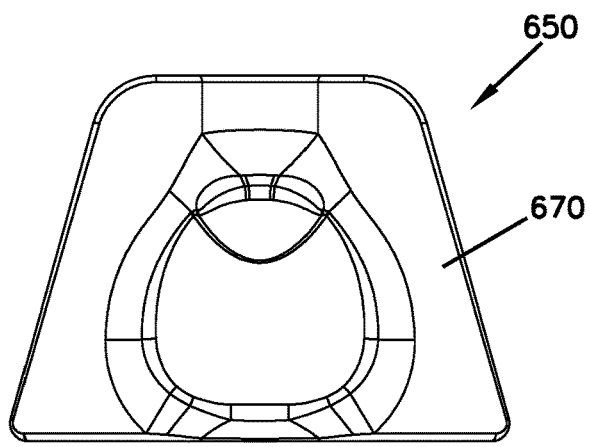
FIG. 44 is a top view of a clip member of the female coupling assembly of FIG. 32.
Figure 45:
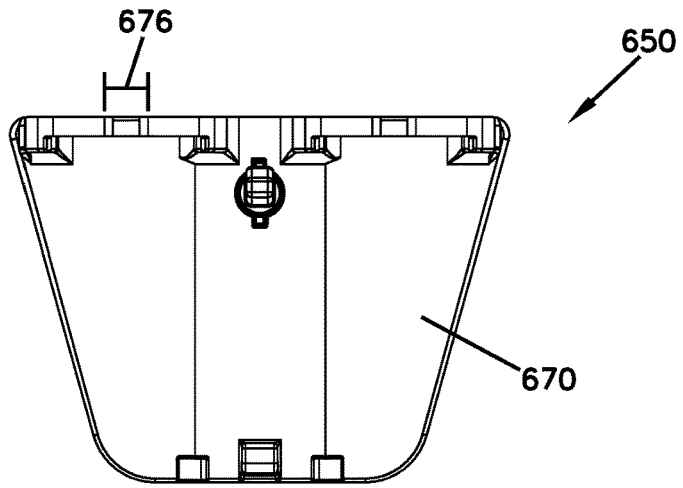
FIG. 45 is a bottom view of the clip member of FIG. 44.
Figure 49:
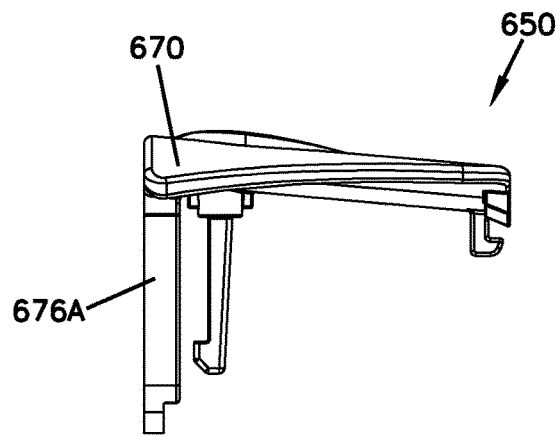
FIG. 49 is a side view of the clip member of FIG. 44.
Figure 46:
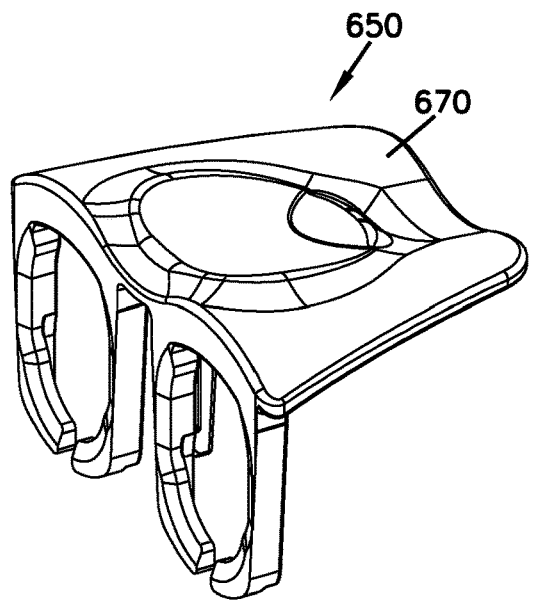
FIG. 46 is a perspective view of the clip member of FIG. 44.
Figure 47:
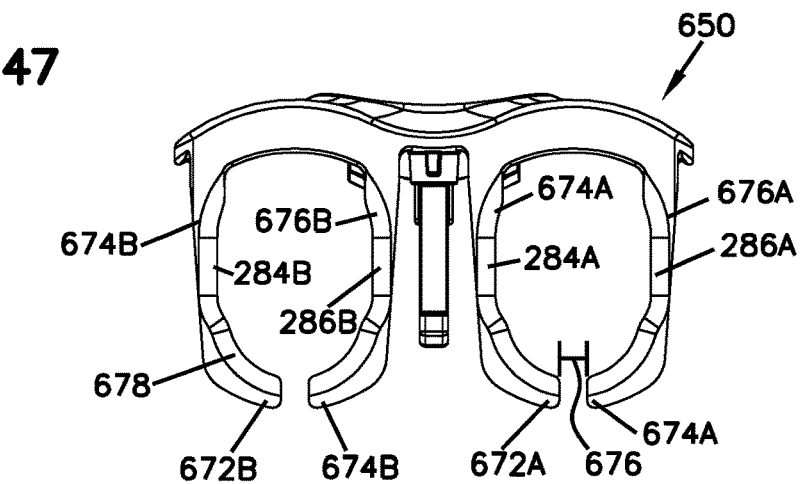
FIG. 47 is an end view of the clip member of FIG. 44.
Figure 48:
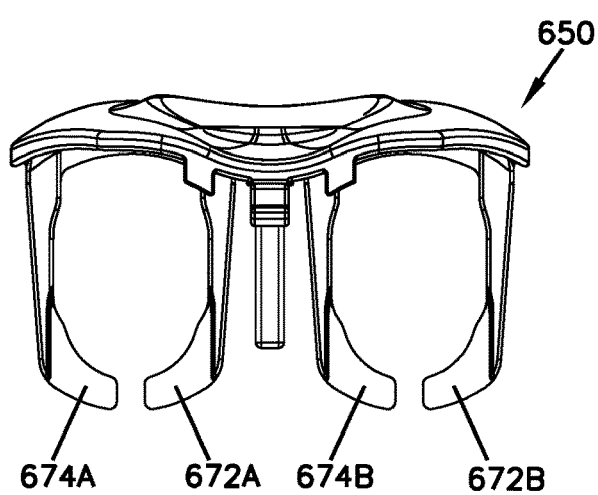
FIG. 48 is an opposite end view of the clip member of FIG. 44.
Figure 50:
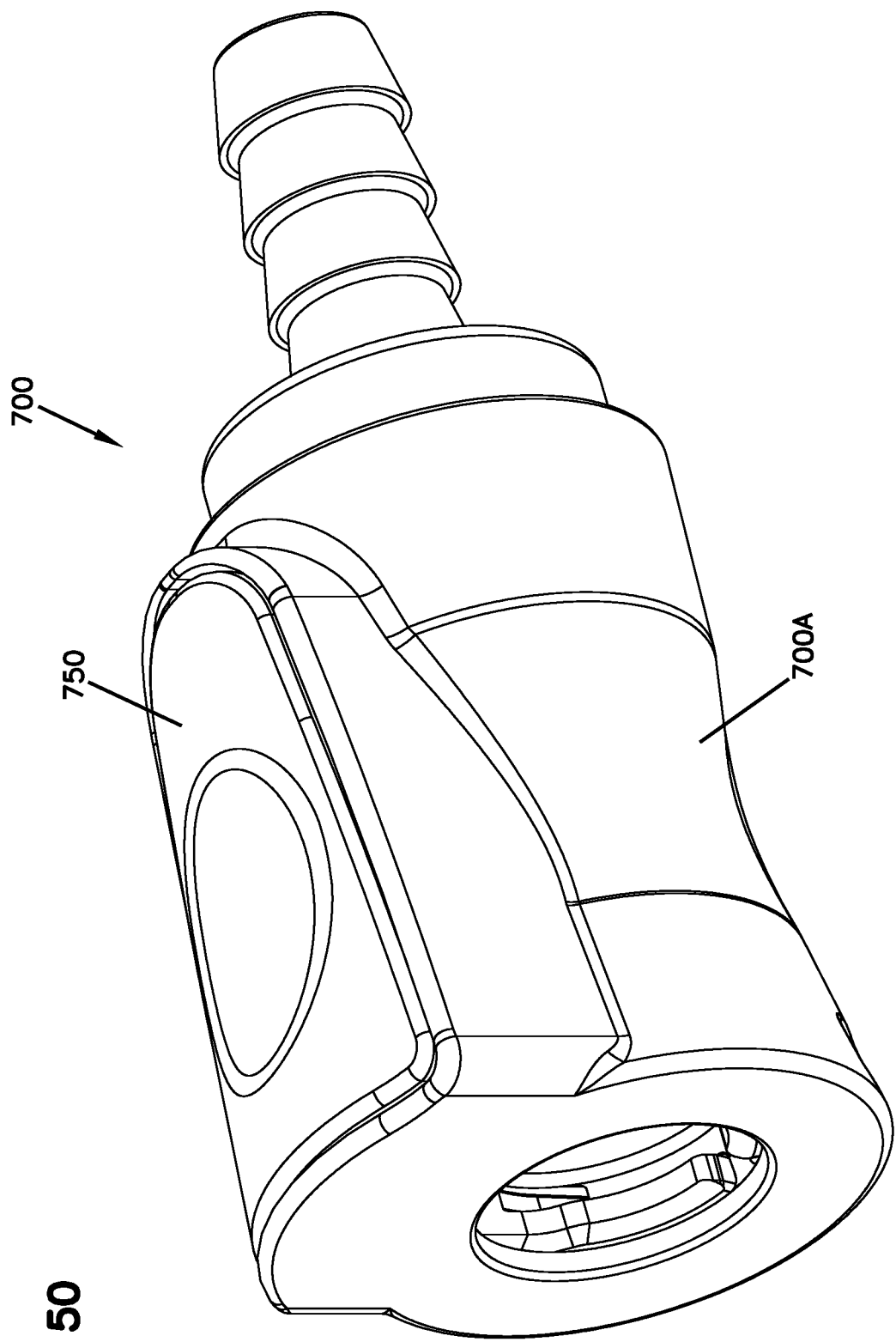
FIG. 50 is a perspective view of another female coupling assembly.
Figure 51:
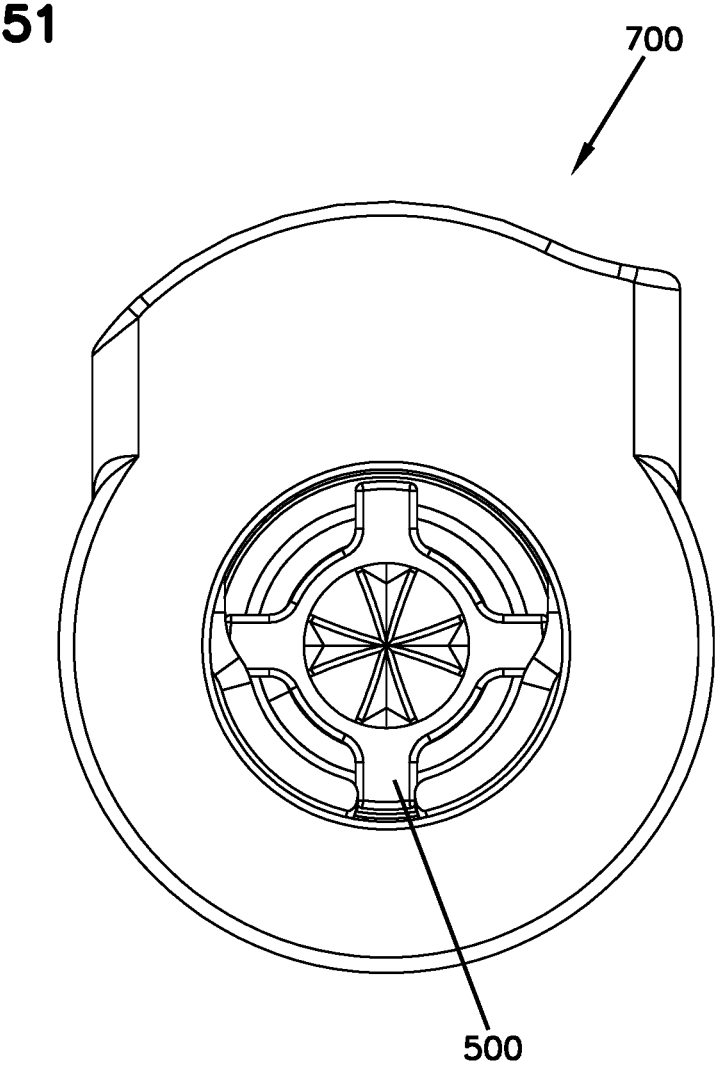
FIG. 51 is an end view of the female coupling assembly of FIG. 50.
Figure 52:
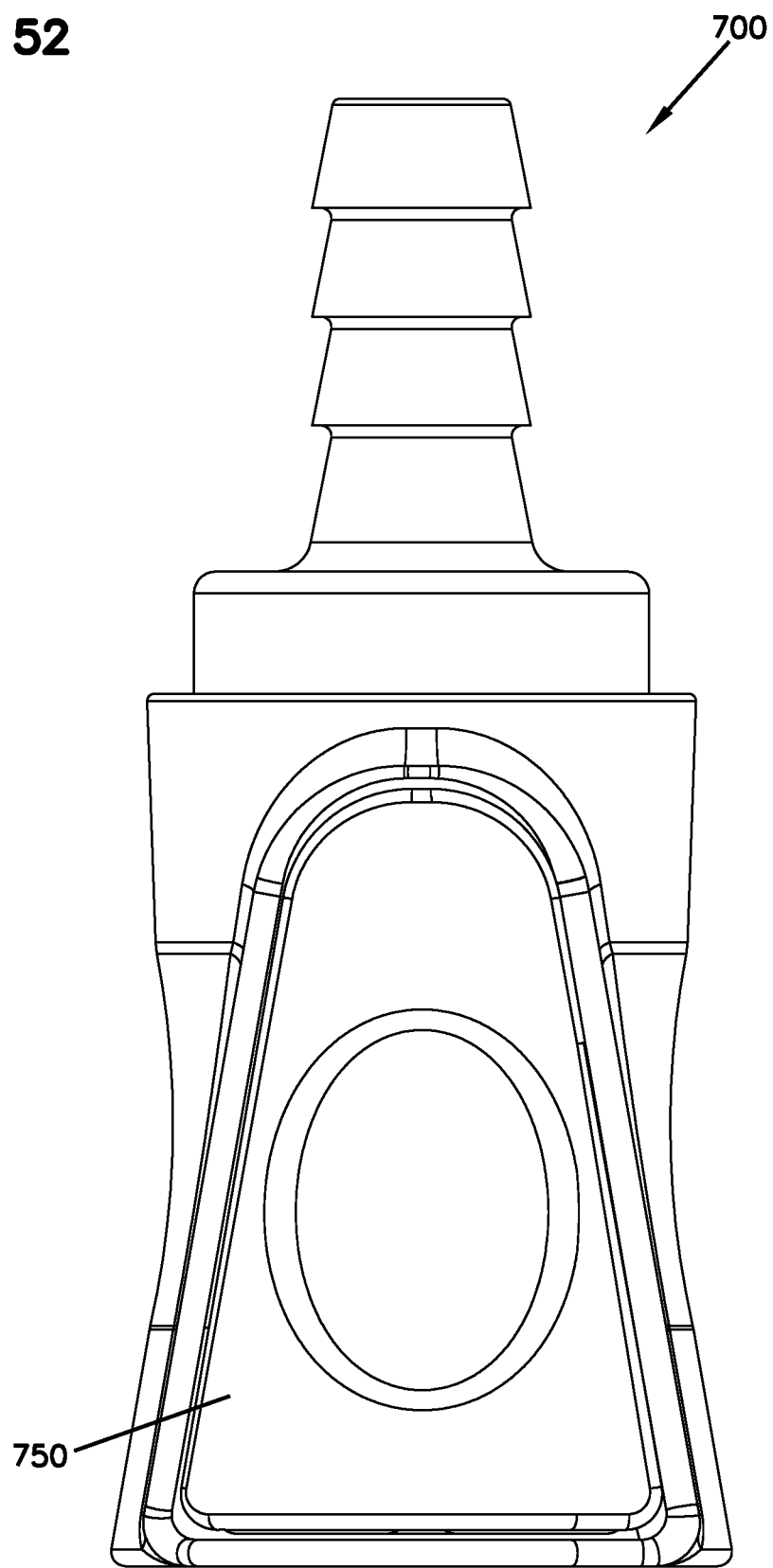
FIG. 52 is a top view of the female coupling assembly of FIG. 50.

When the clip member 650 is depressed, any of the male coupling devices 300A, 300B that is coupled to the female coupling assembly 600 is disconnected from the female coupling assembly 600. When depressed, the arms 674A, 676A (and 674B, 676B) are moved so that notches 284A, 286A, are positioned at the clip groove 303A and the bottom portions 672A, 674A, 672B, 674B are moved out of the clip groove 303A (and move within openings 610 formed at the bottom of the female coupling device 600A, as shown in FIGS. 36 and 42). This allows the front portion 305A to clear the arms 674A, 676A and the bottom portions 672A, 674A, 672B, 674B and thereupon remove the male coupling device 300A from the female coupling device 600A.

A member 611 is formed between each pair of openings 610 formed in the body 600A. The member 611 functions to strengthen the body 600A, particularly during loading of the mating male coupling device upon use. Specifically, the member 611 can maintain the shape of the openings 610 during axial loading of the male coupling device during use.

Although the examples show a dual coupling assembly, in other embodiments a single coupler can be used. In such an example, a single pair of arms would extend from the clip member to capture the single male coupling device inserted into the single female coupling device.

For instance, referring now to FIGS. 50-59, another example female coupling assembly 700 is shown. The female coupling assembly 700 is similar to the female coupling assembly 600 described above except for the noted differences below.

The female coupling assembly 700 includes a single female coupling device 700A and a clip member 750. The female coupling device 700 includes a valve 500.

As shown in FIGS. 55-59, the clip member 750 includes a main body 770 with arms 774A, 774B extend generally perpendicularly from the main body 770 in a pair like clip members 250, 650 described herein.

Each of the arms 774A, 774B includes a bottom portion 772A, 772B that extends from the arms 774A, 774B, respectively. The bottom portion 772A extends towards the bottom portion 772B. Each of the bottom portions 772A, 772B includes a contoured section 778 sized to be received in the clip groove of a mating male coupling device, as described below. The section 778 also assists in the deflection of the arms 774A, 774B during connection of the male coupling device 300A.

The bottom portions 774A, 774B form an opening 776 therebetween, so that the bottom portions 774A, 774B do not extend completely to touch. The opening 776 allows the respective arms 774A, 774B to flex during insertion of the male coupling device, so that the arms 774A, 774B and bottom portions 772A, 772B move outwardly to allow for insertion of the male coupling device 300A. Other configurations are possible. For example, in another design, the bottom portions 774A, 774B extend towards one another to touch or otherwise interface.

When the male coupling device 300A is fully inserted into the female coupling device 700A of the female coupling assembly 700, the arms 774A, 774B are received in the clip groove 303A. In addition, the bottom portions 772A, 772B are received in the clip groove 303A. Since the clip groove 303A has a smaller diameter, the arms 774A, 774B return to their resting positions within the clip groove 303A. In this configuration, the arms 774A, 774B are positioned in the clip groove 303A at opposite sides of the male coupling device 300A and the bottom portions 772A, 772B at the bottom of the clip groove 303A to resist movement of the male coupling device 300A in a direction out of the female coupling device 600A. This retains the male coupling device 300A within the female coupling device 700A so that fluid can flow therethrough.

Figure 53:
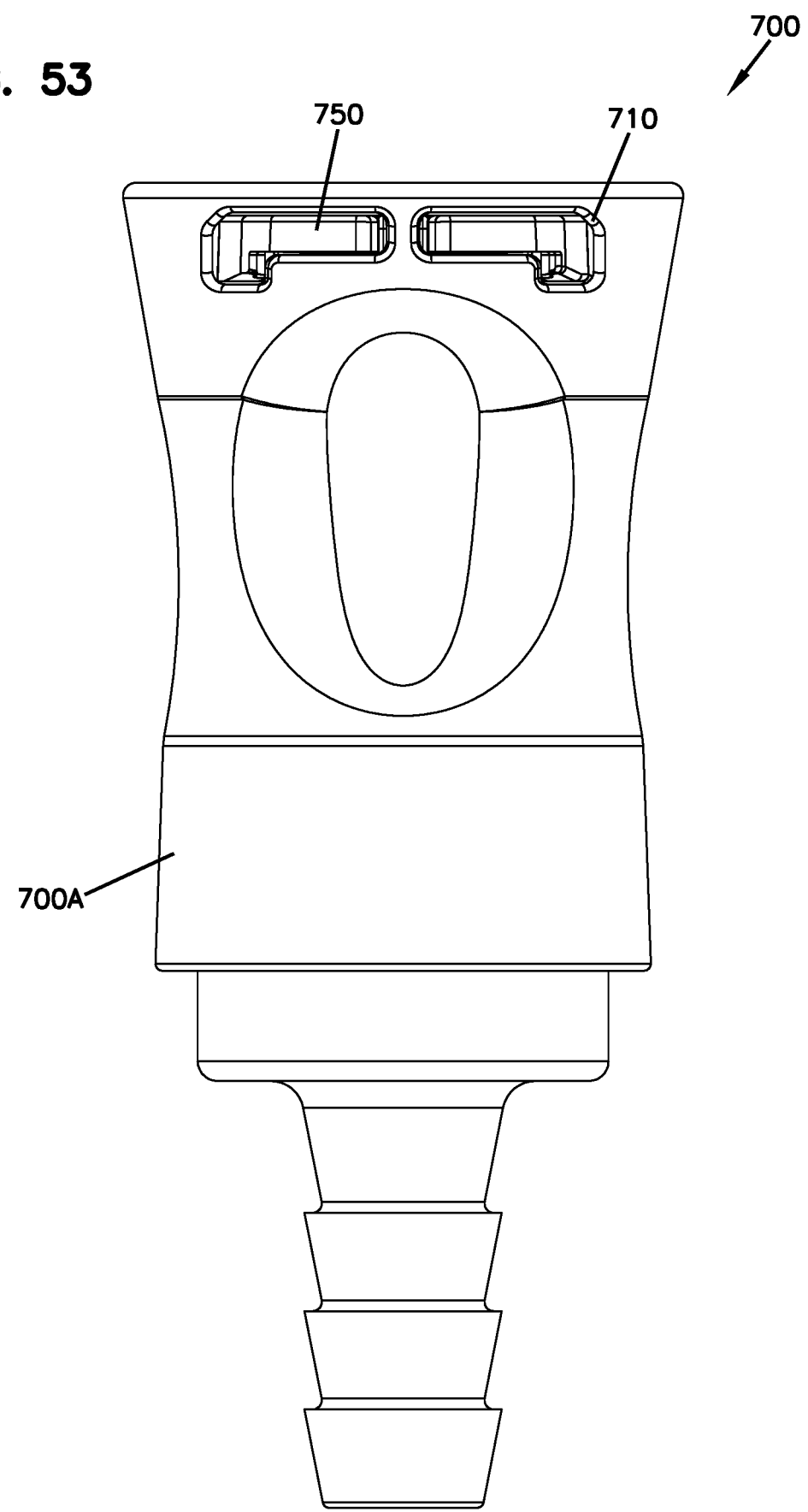
FIG. 53 is a bottom view of the female coupling assembly of FIG. 50.
Figure 54:
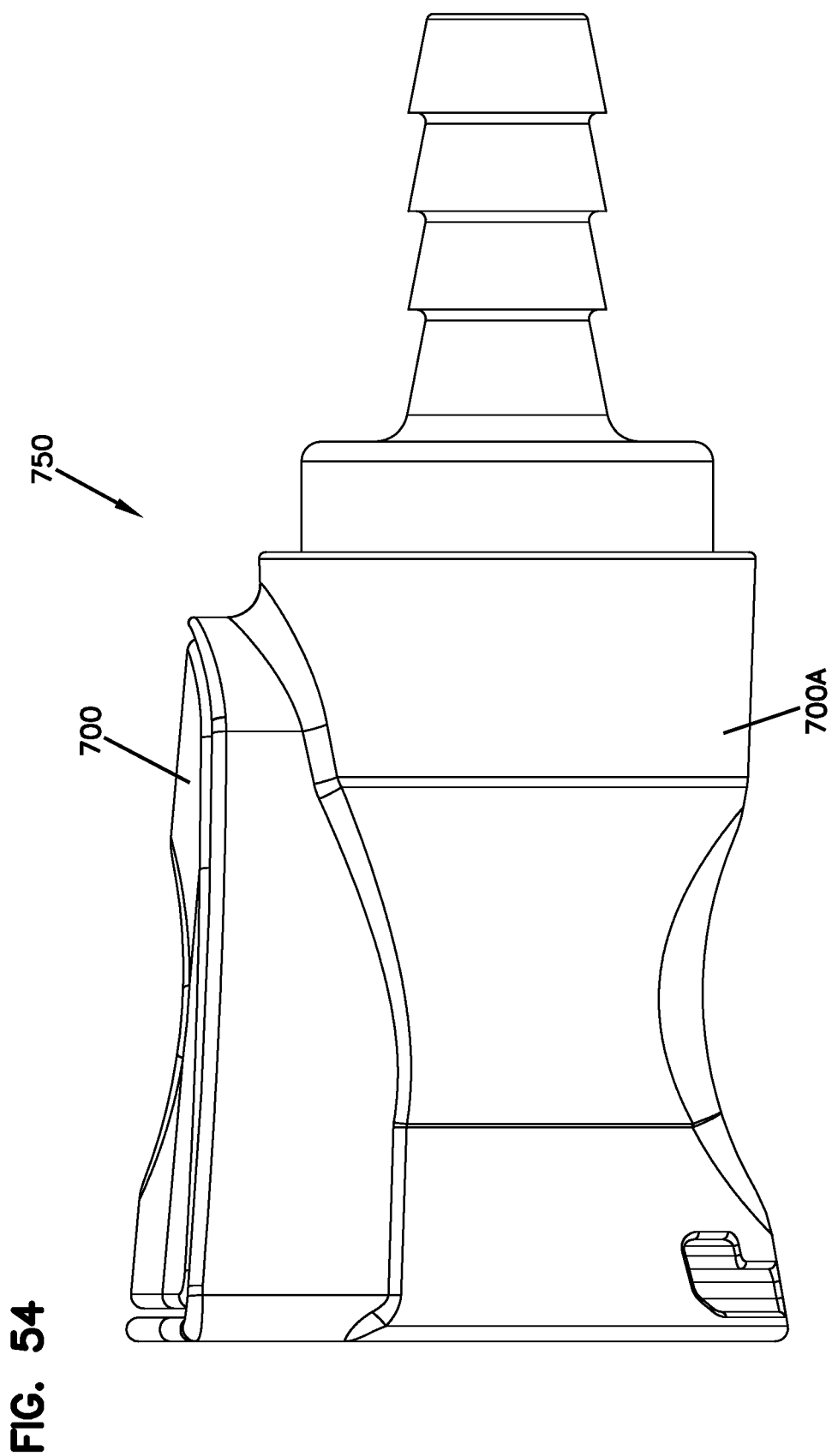
FIG. 54 is a side view of the female coupling assembly of FIG. 50.
Figure 56:
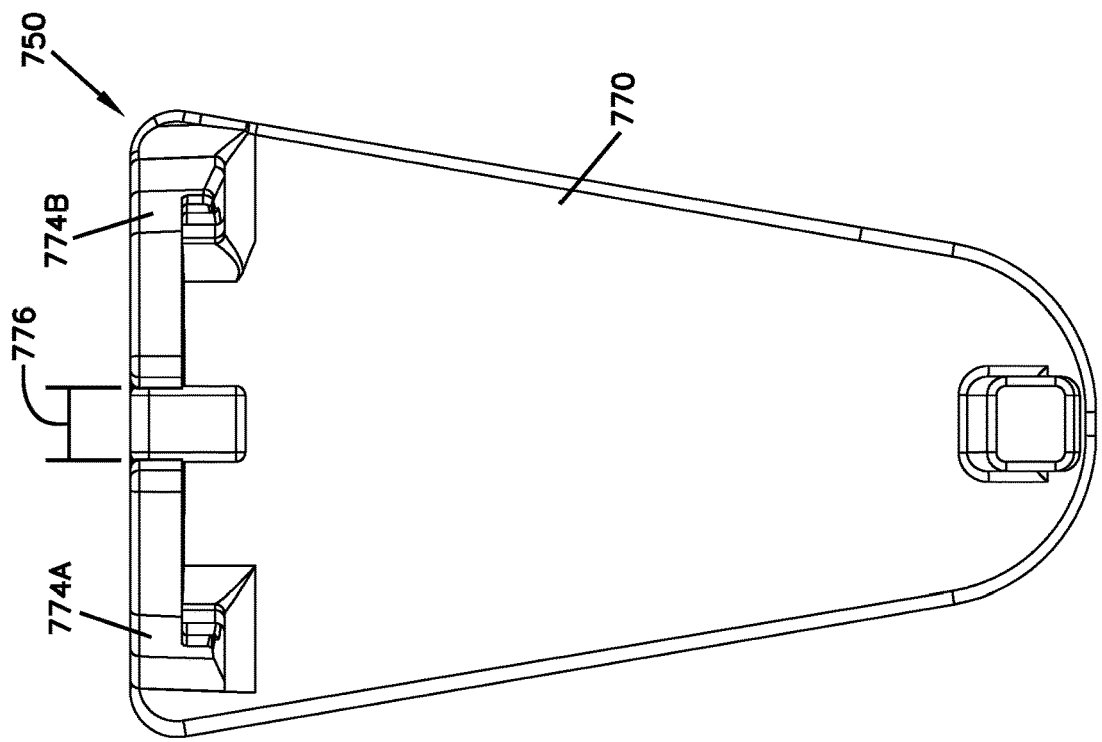
FIG. 56 is a bottom view of the clip member of FIG. 55.
Figure 55:
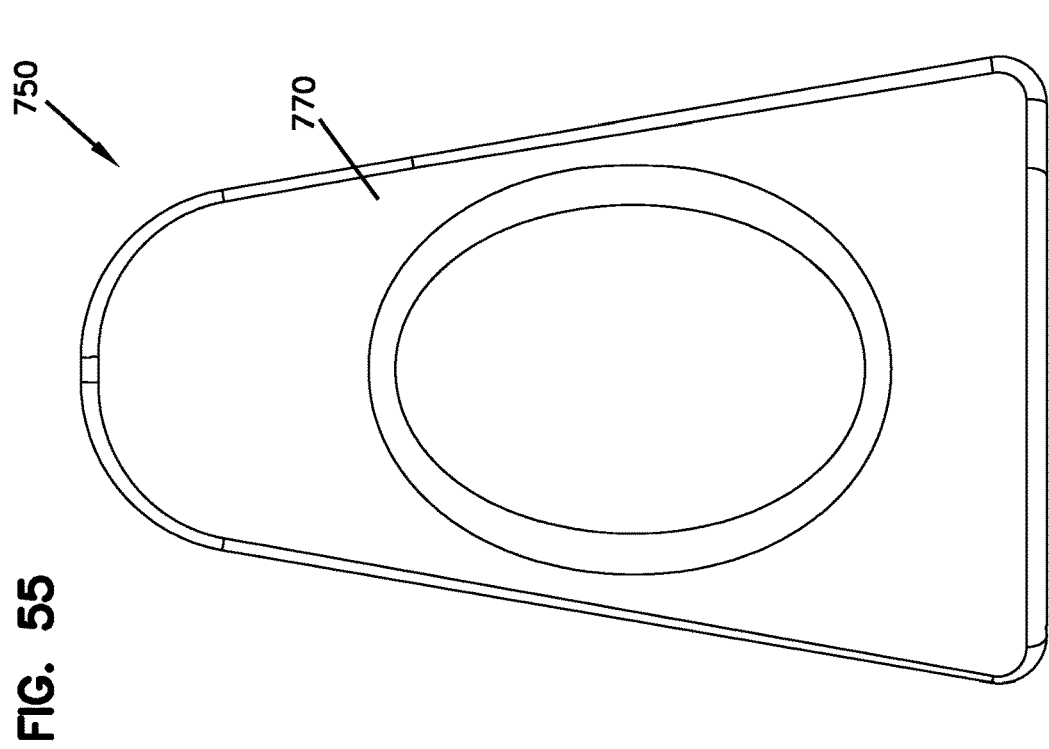
FIG. 55 is a top view of a clip member of the female coupling assembly of FIG. 50.
Figure 57:
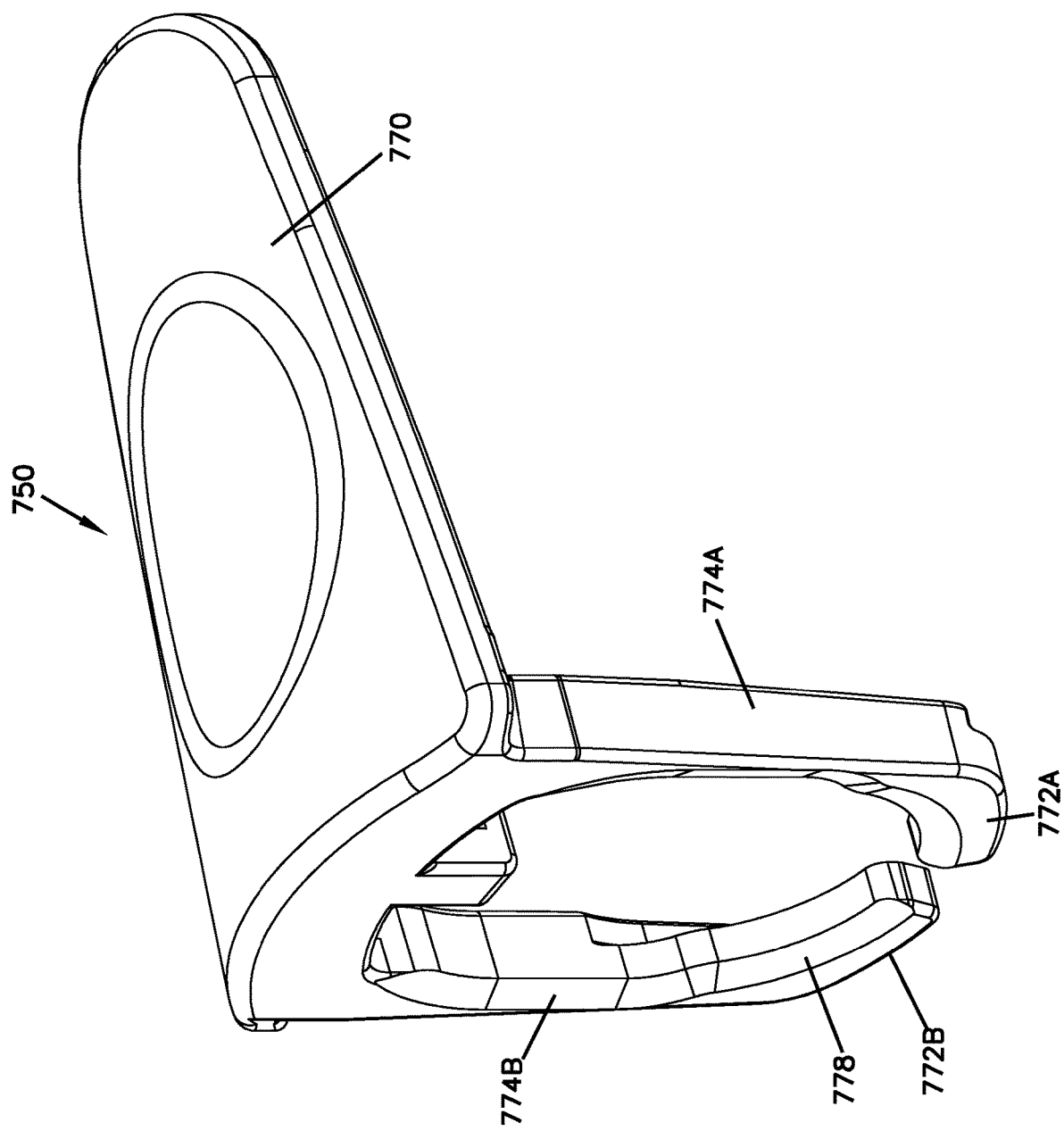
FIG. 57 is a perspective view of the clip member of FIG. 55.
Figure 58:
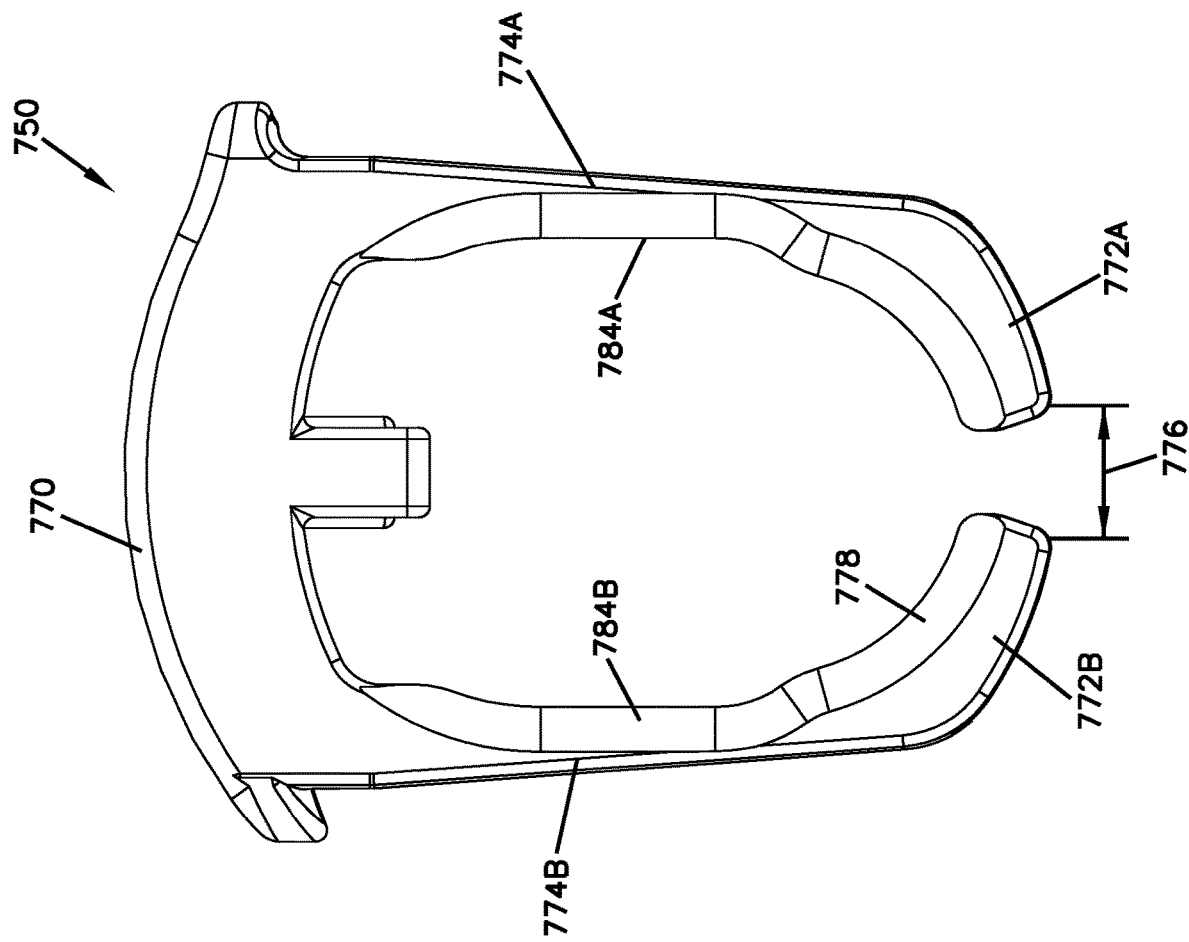
FIG. 58 is an end view of the clip member of FIG. 55.
Figure 59:
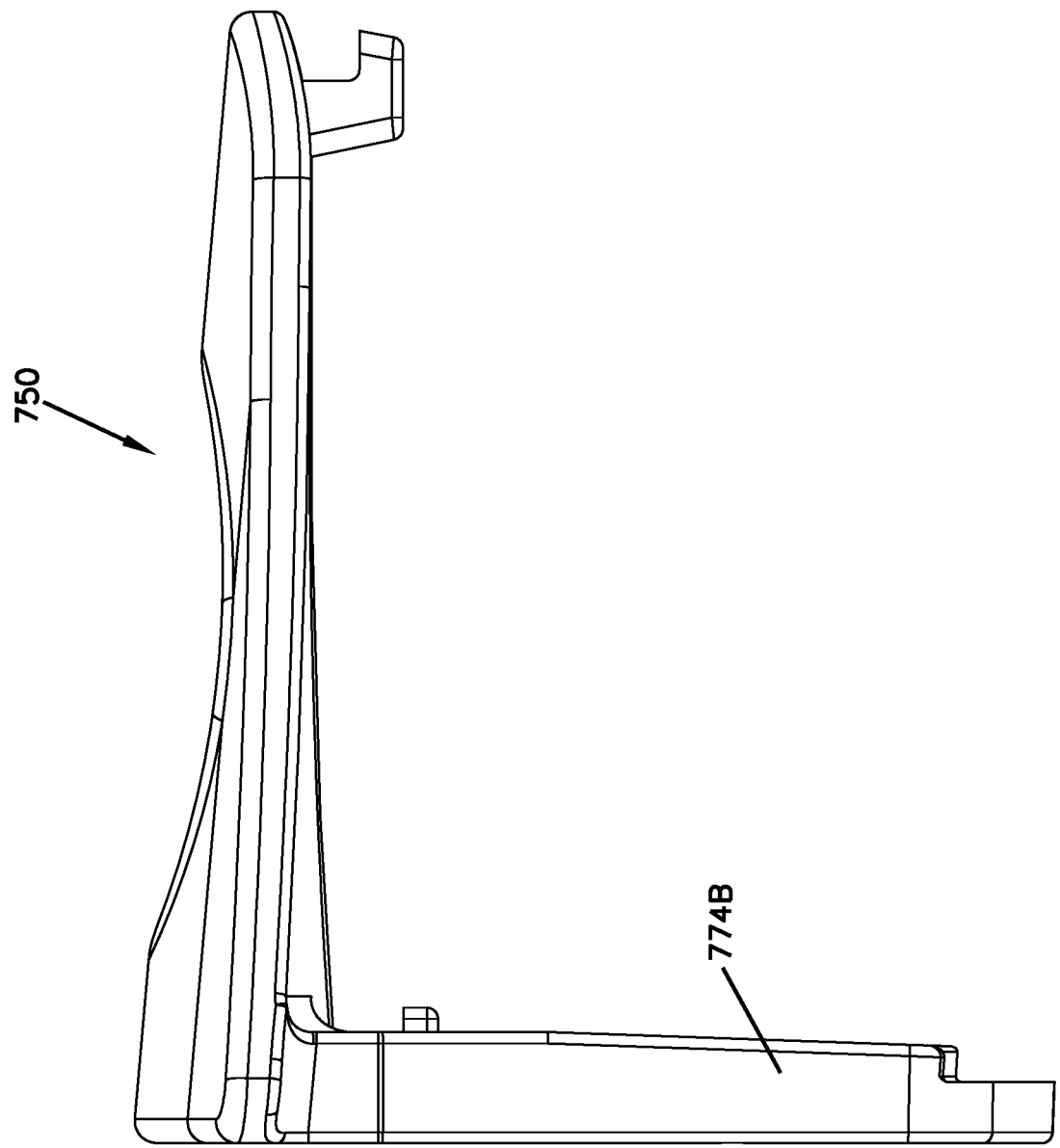
FIG. 59 is a side view of the clip member of FIG. 55.

When the clip member 750 is depressed, the male coupling device 300A that is coupled to the female coupling assembly 700 can be disconnected from the female coupling assembly 700. When depressed, the arms 774A, 774B are moved so that notches 784A, 784B are positioned at the clip groove 303A and the bottom portions 772A, 772B are moved out of the clip groove 303A (and move within openings 710 formed at the bottom of the female coupling device 700A, as shown in FIG. 53). This allows the front portion 305A to clear the arms 774A, 774B and the bottom portions 772A, 772B and thereupon remove the male coupling device 300A from the female coupling device 700A.

Other configurations are possible. For example, in another embodiment, a dual coupling assembly is provided that includes two separate clip members. Each of the clip members can be configured in a manner similar to that of the clip member 750 described above. In this example, each of the clip members of the dual assembly can be actuated separately from the other.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A female coupling device, comprising:
   a main body defining a first fluid passageway extending therethrough along a longitudinal direction of the main body; and
   a clip member coupled to the main body and movable relative to the main body between a locked position and an unlocked position, the clip member comprising a clip body and a pair of arms extending from the clip body transverse to the longitudinal direction,
   wherein a first arm of the pair of arms includes a first bottom end portion and a second arm of the pair of arms includes a second bottom end portion, wherein the first and second bottom end portions are spaced apart from each other by an opening distance,
   wherein the main body defines a first opening in which the first bottom end portion movably resides and a second opening in which the second bottom end portion movably resides,
   wherein an outer wall portion of each of the first and second openings extends at an acute angle relative to the longitudinal direction such that the first and second bottom end portions are forced toward each other by the outer wall portions when the pair of arms are forced in the longitudinal direction against the outer wall portions, wherein the first and second bottom end portions are laterally wider than respective first and second middle portions of the first and second arms, wherein a distance between the first and second middle portions is greater than a distance between the first and second bottom end portions, and wherein inner edges of the first and second bottom end portions are thinner along the longitudinal direction than a thickest portion of the first and second bottom end portions along the longitudinal direction.

2. The female coupling device of claim 1, wherein the main body defines a second fluid passageway extending therethrough along the longitudinal direction of the main body.

3. The female coupling device of claim 2, further comprising a second pair of arms extending from the clip body transverse to the longitudinal direction.

4. The female coupling device of claim 3, wherein the second pair of arms includes a third arm and a fourth arm, and wherein the third arm and the fourth arm are on opposite sides of the second fluid passageway.

5. The female coupling device of claim 4, wherein the main body defines a third opening in which a third bottom end portion of the third arm movably resides and a fourth opening in which the a fourth bottom end portion of the fourth arm movably resides.

6. The female coupling device of claim 5, wherein an outer wall portion of each of the third and fourth openings extends at an acute angle relative to the longitudinal direction such that the third and fourth bottom end portions are forced toward each other by the outer wall portions when the second pair of arms are forced in the longitudinal direction against the outer wall portions.

7. The female coupling device of claim 1, wherein a male coupling device can be coupled with the female coupling device while the clip body remains in the locked position.

8. The female coupling device of claim 7, wherein the first arm and the second arm flex away from each other as the male coupling device is being coupled with the female coupling device.

9. The female coupling device of claim 1, wherein the first arm and the second arm are on opposite sides of the first fluid passageway.

\* \* \* \* \*